United States Patent
Kamiyama et al.

(10) Patent No.: US 8,696,575 B2
(45) Date of Patent: Apr. 15, 2014

(54) ULTRASONIC DIAGNOSTIC APPARATUS AND METHOD OF CONTROLLING THE SAME

(75) Inventors: Naohisa Kamiyama, Otawara (JP); Yoko Okamura, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1308 days.

(21) Appl. No.: 12/178,709

(22) Filed: Jul. 24, 2008

(65) Prior Publication Data

US 2008/0319317 A1 Dec. 25, 2008

Related U.S. Application Data

(63) Continuation of application No. PCT/JP2007/057219, filed on Mar. 30, 2007.

(30) Foreign Application Priority Data

Mar. 31, 2006 (JP) ................................ 2006-100225
May 26, 2006 (JP) ................................ 2006-147265

(51) Int. Cl.
    *A61B 8/00* (2006.01)
(52) U.S. Cl.
    USPC ............ 600/443; 382/190; 600/407; 600/437
(58) Field of Classification Search
    USPC .......... 600/443; 382/130, 165, 190, 194, 195, 382/199, 203
    See application file for complete search history.

(56) References Cited

U.S. PATENT DOCUMENTS

| | | | |
|---|---|---|---|
| 4,016,751 A * | 4/1977 | Kossoff ........................... | 73/641 |
| 6,155,978 A | 12/2000 | Cline et al. | |
| 6,620,103 B1 * | 9/2003 | Bruce et al. ................... | 600/458 |
| 2004/0073112 A1 | 4/2004 | Azuma et al. | |
| 2005/0131295 A1* | 6/2005 | Li ................................. | 600/443 |
| 2005/0143655 A1 | 6/2005 | Satoh | |
| 2006/0173324 A1 | 8/2006 | Cohen-Bacrie et al. | |

FOREIGN PATENT DOCUMENTS

| | | |
|---|---|---|
| JP | 61-189476 A | 8/1986 |
| JP | 2000-279416 A | 10/2000 |
| JP | 2001-238884 A | 9/2001 |
| JP | 2002-102223 A | 4/2002 |
| JP | 2003-61964 A | 3/2003 |
| JP | 2003-61964 A | 3/2004 |

(Continued)

OTHER PUBLICATIONS

U.S. Appl. No. 12/484,465, filed Jun. 15, 2009, Okamura, et al.

(Continued)

*Primary Examiner* — Unsu Jung
*Assistant Examiner* — Saurel J Selkin
(74) *Attorney, Agent, or Firm* — Oblon, Spivak, McClelland, Maier & Neustadt, L.L.P.

(57) ABSTRACT

An ultrasonic diagnostic apparatus removes a speckle pattern using information on a direction (depth direction) that is substantially orthogonal to a plurality of ultrasonic images included in three-dimensional image data. For example, three-dimensional CFAR processing, two-dimensional CFAR processing, and a depth-direction arithmetic process are performed to discriminate a continuous structure that is three-dimensionally arranged from a local microstructure, thereby generating a microstructure extracted image.

25 Claims, 20 Drawing Sheets

(56) References Cited

FOREIGN PATENT DOCUMENTS

| | | |
|---|---|---|
| JP | 2004-129773 A | 4/2004 |
| JP | 3596792 | 9/2004 |
| JP | 2004-321582 A | 11/2004 |
| JP | 2005-205199 A | 8/2005 |
| WO | WO 2004/081864 A2 | 9/2004 |

OTHER PUBLICATIONS

Tadashi Yamaguchi, et al., "Extraction of Quantitative Three-Dimensional Information from Ultrasonic Volumetric Images of Cirrhotic Liver", Japan Journal of Applied Physics, vol. 39, Part 1, No. 5B, May 2000, pp. 3266-3269.

* cited by examiner

ULTRASONIC DIAGNOSTIC APPARATUS AND METHOD OF CONTROLLING THE SAME

CROSS REFERENCE TO RELATED APPLICATIONS

This is a Continuation Application of PCT Application No. PCT/JP2007/057219, filed Mar. 30, 2007, which was published under PCT Article 21(2) in Japanese.

This application is based upon and claims the benefit of priority from prior Japanese Patent Applications No. 2006-100225, filed Mar. 31, 2006; and No. 2006-147265, filed May 26, 2006, the entire contents of both of which are incorporated herein by reference.

BACKGROUND OF THE INVENTION

1. Field of the Invention

The present invention relates to an ultrasonic diagnostic apparatus that extracts microstructures from internal organs on the basis of echo signals from tissue, and a method of controlling the same.

2. Description of the Related Art

Ultrasonic diagnosis makes it possible to display how the heart beats or the embryo moves in real time by a simple operation of tapping an ultrasonic probe on the body surface, and allows repetitive examination because it is highly safe. In addition, the size of an ultrasonic diagnostic system is smaller than other diagnostic apparatuses, such as X-ray, CT, and MRI apparatuses, and the apparatus can be moved to a bed side to allow easy examination. Ultrasonic diagnostic apparatuses used for the ultrasonic diagnosis vary depending on the types of functions which they have. For example, an ultrasonic diagnostic apparatus having a size that allows an operator to carry it with his/her one hand has been developed, and ultrasonic diagnosis is free from the influence of radiation exposure such as X-ray exposure. Therefore, the ultrasonic diagnostic apparatus can be used in obstetrical treatment, treatment at home, and the like.

This type of ultrasonic diagnosis includes breast cancer early diagnosis. It has been known that, in many cases, micro calcification occurs in breast tissue as a symptom of breast cancer. One or a few calcified lesions are scattered in local portions. Since lime is harder than living tissue, it reflects ultrasonic waves well. Therefore, such a calcified lesion is expected to exhibit high brightness on an image. However, it is difficult to extract such a lesion from an image by visual recognition even if it has a size of about several hundreds of microns.

In some cases, interference fringes called speckle patterns due to random interference between ultrasonic waves are generated on an ultrasonic image. On the other hand, this speckle pattern is used to diagnose, for example, hapatocirrhosis. For example, this speckle pattern is very similar to a microstructure such as a micro calcified substance which tends to be overlooked in, for example, the above breast cancer diagnosis. In some cases, the speckle pattern becomes misleading image information. For this reason, in the above breast cancer diagnosis which requires no speckle pattern, in order to remove the speckle pattern, for example, the following processing is performed: spatial compounding, CFAR (contrast false alarm rate) processing, and a similarity filtering process. The spatial compounding is to overlap signals that are transmitted or received in different directions and smooth the speckle pattern. The CFAR processing is to subtract a target pixel from the average brightness of adjacent pixels of the target pixel and extract a high-brightness portion on the basis of the difference. The similarity filtering process is to remove the speckle pattern using its statistical property. These techniques are disclosed in, for example, Japanese Unexamined Patent Application Publication Nos. 61-189476, 2001-238884, 2003-61964, and 2004-321582. Although not included in the ultrasonic diagnosis field, in addition to these techniques for removing the speckle pattern, various attempts to automatically recognize micro calcification have been reported mainly as applications of X-ray diagnostic images (for example, Japanese Patent No. 3596792).

Further, an MIP process has been proposed as another technique for extracting a microstructure, such as micro calcified substance. The MIP process projects a representative value, which is the maximum brightness of a plurality of image frames, onto one frame. The MIP process is mainly used to display volume data as a two-dimensional image during three-dimensional image processing. Ideally, it is possible to superpose information of a plurality of frames on one frame to obtain an image having a large amount of information. Further, it is also possible to change image quality adjusting parameters provided in an ultrasonic diagnostic apparatus according to the related art to reduce the speckle pattern. Furthermore, for example, when a dynamic range is narrowed, only specific signals in a narrow range are displayed. When optimum setting, such as the setting of low gain, is performed, it is possible to display only microstructures having relatively high signal intensity without displaying the speckle pattern having relatively low signal intensity.

However, for example, the following problems arise in the above conventional techniques for extracting microstructures.

For example, the mammary gland, which is a diagnosis target, is an internal organ that has a complicated structure of breast duct and the like and is not homogeneous. Therefore, when the filtering process according to the related art is performed, both a micro calcified substance and the mammary gland are extracted (as structures), and the operator is difficult to clearly discriminate them.

Further, for example, a breast duct is significantly larger than a micro calcified substance, it is expected that the operator will discriminate the breast duct from other substances by eyes after the filtering process. However, the inventors' studies proved that the filtering process was insufficient to clearly discriminate the breast duct from other substances. In particular, when a portion of the mammary gland structure remains, a filter image seems to be a dot, which is similar to the image of a micro calcified substance.

BRIEF SUMMARY OF THE INVENTION

The invention has been made to solve the above-mentioned problems, and an object of the invention is to provide an ultrasonic diagnostic apparatus capable of exactly discriminating a continuous microstructure, such as the mammary gland, from a microstructure, such as a micro calcified portion, to extract the microstructure, and a method of controlling the ultrasonic diagnostic apparatus.

According to a first aspect of the invention, an ultrasonic diagnostic apparatus includes: an ultrasonic wave transmitting/receiving unit that transmits an ultrasonic wave to a subject, receives a reflected wave of the ultrasonic wave, and generates echo signals of a plurality of frames on the basis of the received reflected wave; an image data generating unit that generates three-dimensional image data composed of a plurality of two-dimensional images on the basis of the echo signals of the plurality of frames; an image generating unit that generates a first image by performing a process of enhancing a microstructure included in the three-dimensional image data; and a display unit that displays the first image.

According to a second aspect of the invention, there is provided a method of controlling an ultrasonic diagnostic apparatus. The method includes: allowing the ultrasonic diagnostic apparatus to transmit an ultrasonic wave to a subject, receive a reflected wave of the ultrasonic wave, generate echo signals of a plurality of frames on the basis of the received reflected wave, generate three-dimensional image data composed of a plurality of two-dimensional images on the basis of the echo signals of the plurality of frames, generate a first image by performing a process of enhancing a microstructure included in the three-dimensional image data, and display the first image.

DETAILED DESCRIPTION OF THE INVENTION

Figure 1:
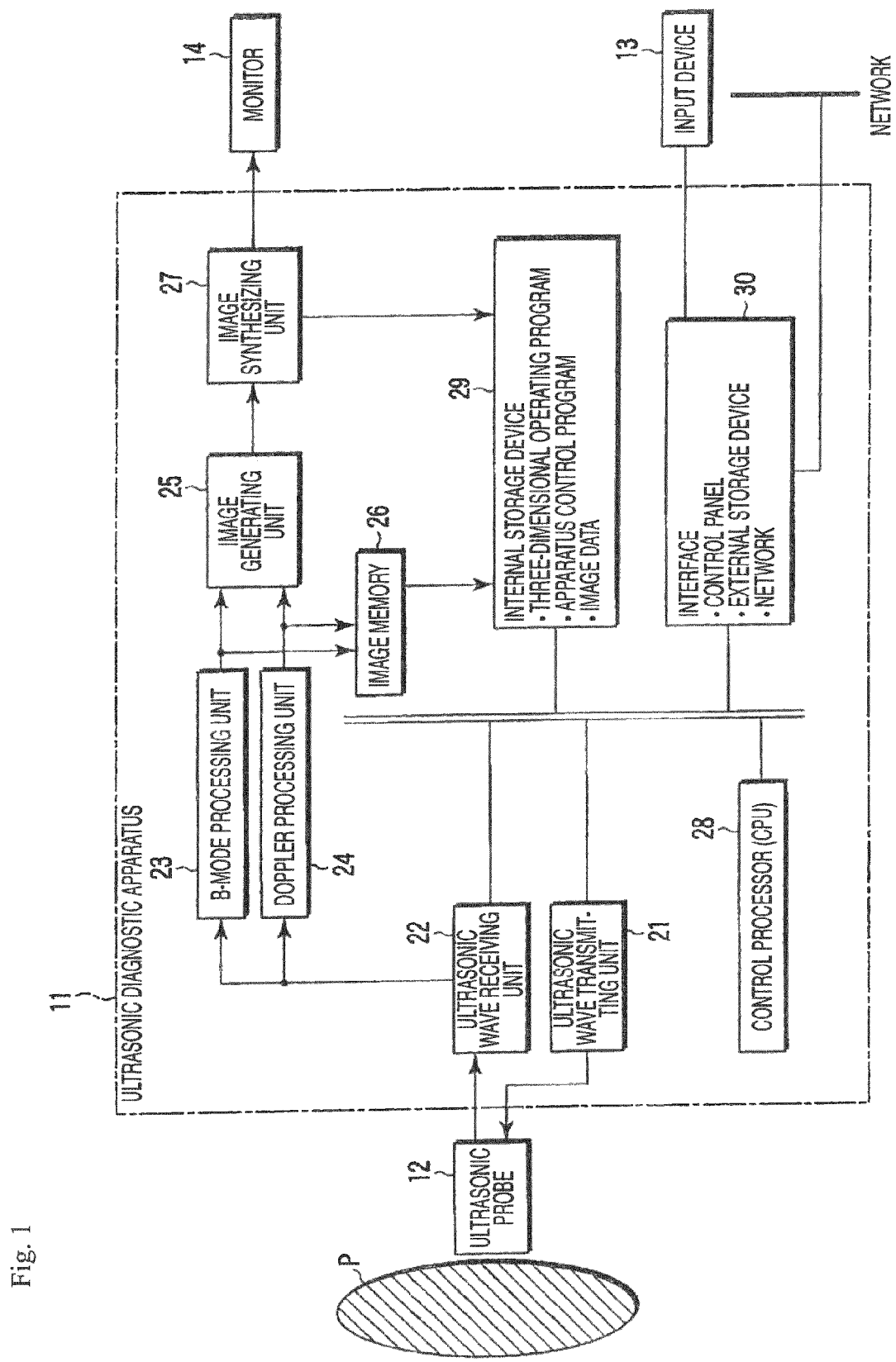
FIG. 1 is a block diagram illustrating the structure of an ultrasonic diagnostic apparatus according to a first embodiment of the invention.

Hereinafter, first to seventh embodiments of the invention will be described with reference to the accompanying drawings. In the following description, components having substantially the same function and structure are denoted by the same reference numerals, and a repetitive description thereof will be made, if necessary.

(First Embodiment)

FIG. 1 is a block diagram illustrating the structure of an ultrasonic diagnostic apparatus according to a first embodiment of the invention. As shown in FIG. 1, an ultrasonic diagnostic apparatus 11 according to this embodiment includes an ultrasonic probe 12, an input device 13, a monitor 14, an ultrasonic wave transmitting unit 21, an ultrasonic wave receiving unit 22, a B-mode processing unit 23, a Doppler processing unit 24, an image generating unit 25, an image memory 26, an image synthesizing unit 27, a control processor (CPU) 28, an internal storage unit 29, and an interface 30. Hereinafter, the functions of the components will be described.

The ultrasonic probe 12 includes a plurality of piezoelectric vibrators that generate ultrasonic waves on the basis of a driving signal from the ultrasonic wave transmitting unit 21 and convert reflected waves from a subject into electric signals, a matching layer that is provided in each of the piezoelectric vibrators, and a backing member that prevents ultrasonic waves from being propagated to the rear side of the piezoelectric vibrators. When ultrasonic waves are transmitted from the ultrasonic probe 12 to a subject P, the transmitted ultrasonic waves are sequentially reflected from a discontinuous surface of the acoustic impedance of tissue in the body and are input to the ultrasonic probe 12 as echo signals. The amplitude of the echo signal depends on a difference in the acoustic impedance of the discontinuous surface from which the ultrasonic wave is reflected. When the transmitted ultrasonic wave is reflected from blood flowing in the blood vessels or a cardiac wall, the echo signal depends on a speed component of an object flowing in the direction in which ultrasonic waves are transmitted by the Doppler effect, and a frequency shift occurs in the echo signal.

The ultrasonic probe 12 provided in the ultrasonic diagnostic apparatus according to this embodiment can scan a three-dimensional region of a subject with ultrasonic waves. Therefore, the ultrasonic probe 12 has a structure in which the vibrators are mechanically tilted in a direction orthogonal to the direction in which they are arranged to scan the three-dimensional area with ultrasonic waves or a structure in which two-dimensional vibrators that are two-dimensionally arranged are electrically controlled to scan a three-dimensional region with ultrasonic waves. When the former structure is used, the three-dimensional scanning of the subject is performed by a tilting circuit. Therefore, it is possible to automatically obtain a plurality of two-dimensional tomographic images of the subject by only contacting a probe body with the subject. It is also possible to measure the exact distance between the tomographic images from the controlled tilting speed. When the latter structure is used, theoretically, it is possible to scan a three-dimensional region with ultrasonic waves at the same time as that required to obtain a two-dimensional tomographic image in the related art.

The input device 13 is connected to the ultrasonic diagnostic apparatus 11, and includes various types of switches, buttons, a track ball, a mouse, and a keyboard that input to the apparatus body 11, for example, various instructions from an operator, instructions to set conditions and a region of interest (ROI), and instructions to set various image quality conditions. For example, when the operator pushes an end button or a FREEZE button of the input device 13, the transmission or reception of an ultrasonic wave ends, and the ultrasonic diagnostic apparatus stops temporarily.

The monitor 14 displays morphological information (B-mode image) of a living body, blood flow information (for example, an average speed image, a dispersed image, and a power image), and a combination thereof as images, on the basis of video signals from the scan converter 25.

An external storage device 16 is a recording medium, such as a magnetic disk (for example, a floppy (registered trademark) disk or a hard disk) or an optical disk (for example, CD-ROM or DVD), or a semiconductor memory, and reads information recorded on the recording media. The information read from various kinds of recording media is transmitted to the control processor 28 through the interface 30.

The ultrasonic wave transmitting unit 21 includes, for example, a trigger generating circuit, a delay circuit, and a pulsar circuit (all of which are not shown in the drawings). The pulsar circuit repeatedly generates a rate pulse used to form an ultrasonic wave at a predetermined rate frequency of fr Hz (period: 1/fr second). The delay circuit assigns to each rate pulse a delay time required to focus an ultrasonic wave in a beam shape and determine the transmission directivity for each channel. The trigger generating circuit applies a driving pulse to the ultrasonic probe 12 at the timing based on the rate pulse.

Further, in order to perform a predetermined scan sequence under the control of the control processor 28, the ultrasonic wave transmitting unit 21 has a function of instantaneously changing, for example, a transmission frequency and a transmission driving voltage. In particular, the transmission driving voltage is changed by a linear amplifier type transmitting circuit capable of switching its values instantaneously or a mechanism that electrically switches a plurality of power supply units.

The ultrasonic wave receiving unit 22 includes, for example, an amplifier circuit, an analog-to-digital (A/D) converter, and an adder (which are not shown in the drawings). The amplifier circuit has a function of amplifying the echo signal received by the ultrasonic probe 12 for each channel. The analog-to-digital converter assigns to the amplified echo signal a delay time that is required to determine reception directivity. The adder has a function to perform addition processing on the echo signal transmitted from the analog-to-digital converter. The addition processing enhances reflective components of the echo signals in a direction corresponding to the reception directivity, and the reception directivity and the transmission directivity form an integrated beam for ultrasonic transmission and reception.

The B-mode processing unit 23 receives the echo signal from the —transmitting/receiving unit 21 and performs various processes, such as a logarithmic amplification process, and an envelope detection process, and generates data whose signal intensity is represented by brightness. The data is transmitted to the scan converter 25 and then displayed on the monitor 14 as a B-mode image in which the intensity of a reflected wave is represented by brightness.

The Doppler processing unit 24 performs frequency analysis on velocity information from the echo signal received from the transmitting/receiving unit 21, and extracts a blood flow, tissues, and contrast medium echo components using the Doppler effect to obtain blood flow information, such as the average velocity, dispersion, and power, at a number of points.

The image generating unit 25 generally converts (scan-converts) a scanning line signal string for ultrasonic scanning into a scanning line signal string of a general video format, which is a representative format for TV signals, thereby generating an ultrasonic diagnostic image as a displayed image.

Further, the image generating unit 25 performs various types of image processing other than the scan conversion. That is, the image generating unit 25 performs, for example, a process of extracting a microstructure, which will be described below, a method of using a plurality of image frames subjected to the scan conversion to reproduce an image with an average brightness value (a smoothing process), a method of using a differential filter in an image (edge enhancement), a volume rendering process of using a three-dimensional reconstruction algorithm (three-dimensional image reconstruction), and a method of a difference between images (difference operation). In addition, data before being input to the image generating unit 25 is called 'raw data'.

The image memory (cine memory) 26 is a storage unit that stores ultrasonic images corresponding to a plurality of frames immediately before freezing. It is possible to display ultrasonic images by continuously displaying (cine display) the images stored in the image memory 26.

The image synthesizer 27 synthesizes the image received from the image generating unit 25 with character information of various parameters and scales and outputs the synthesized image as video signals to the monitor 14.

The control processor 28 has the function of an information processing device (a computer), and controls the operation of the ultrasonic diagnostic apparatus according to this embodiment. The control processor 28 reads a dedicated program for implementing a microstructure extracting function and a control program for generating and displaying a predetermined image from the internal storage unit 29, expands the read programs on its own memory, and performs arithmetic and control operations related to various processes.

The internal storage unit 29 stores a scan sequence, a dedicated program for implementing the microstructure extracting function according to this embodiment, control programs for executing the generation and display of images, programs for controlling diagnostic information (for example, patient IDs and observations of doctors), diagnostic protocols, transmission and reception conditions of ultrasonic waves, CFAR processing program, body mark producing program, and other data groups. The internal storage unit 29 is also used to store image data in the image memory 26, if necessary. Data stored in the internal storage unit 29 may be transmitted to external peripheral apparatuses through the interface circuit 30.

The interface 30 is for the input device 13, a network, and a new external storage device (not shown). For example, data of the ultrasonic images and the analysis results obtained by the ultrasonic diagnostic apparatus may be transmitted to another apparatuses through the interface 30 over a network.

(Microstructure Extracting Function)

Next, the microstructure extracting function of the ultrasonic diagnostic apparatus 1 according to this embodiment will be described. Essentially, a microstructure that locally exists in one place, such as a micro calcified portion, is greatly different from a continuous structure that is three-dimensionally continuous in a predetermined range, such as the mammary gland, in that the shape of spatial distribution. The invention has been made paying attention to the difference. That is, for example, in the diagnosis of the breast, the liver, and the pancreas, the invention discriminates the two microstructures on the basis of the shape of spatial distribution, and generates an image on which a microstructure is clearly extracted (microstructure extracted image).

In this embodiment, for clarity of description, CFAR processing is used as a method of removing a speckle pattern from a B-mode image. However, the invention is not limited thereto. For example, the following methods may be used: a spatial compounding method of overlapping signals transmitted or received in different directions to smooth the speckle pattern; and a similarity filtering method of using a statistical property to remove the speckle pattern. The term 'CFAR processing' is used in the radar field. In this embodiment, for clarity of description, the CFAR processing is referred to as 'CFAR' for the sake of convenience. However, the invention is not limited to a method that is used in the radar field or a method of strictly using statistics.

Further, a process (microstructure extracting process) using the microstructure extracting function according to this embodiment is performed on three-dimensional image data. The term 'three-dimensional image data' means volume data having a plurality of two-dimensional images or data composed of a plurality of different two-dimensional images (which do not necessarily form complete volume data). In this embodiment, for clarity of description, a microstructure extracting process using the volume data will be described.

Figure 2:
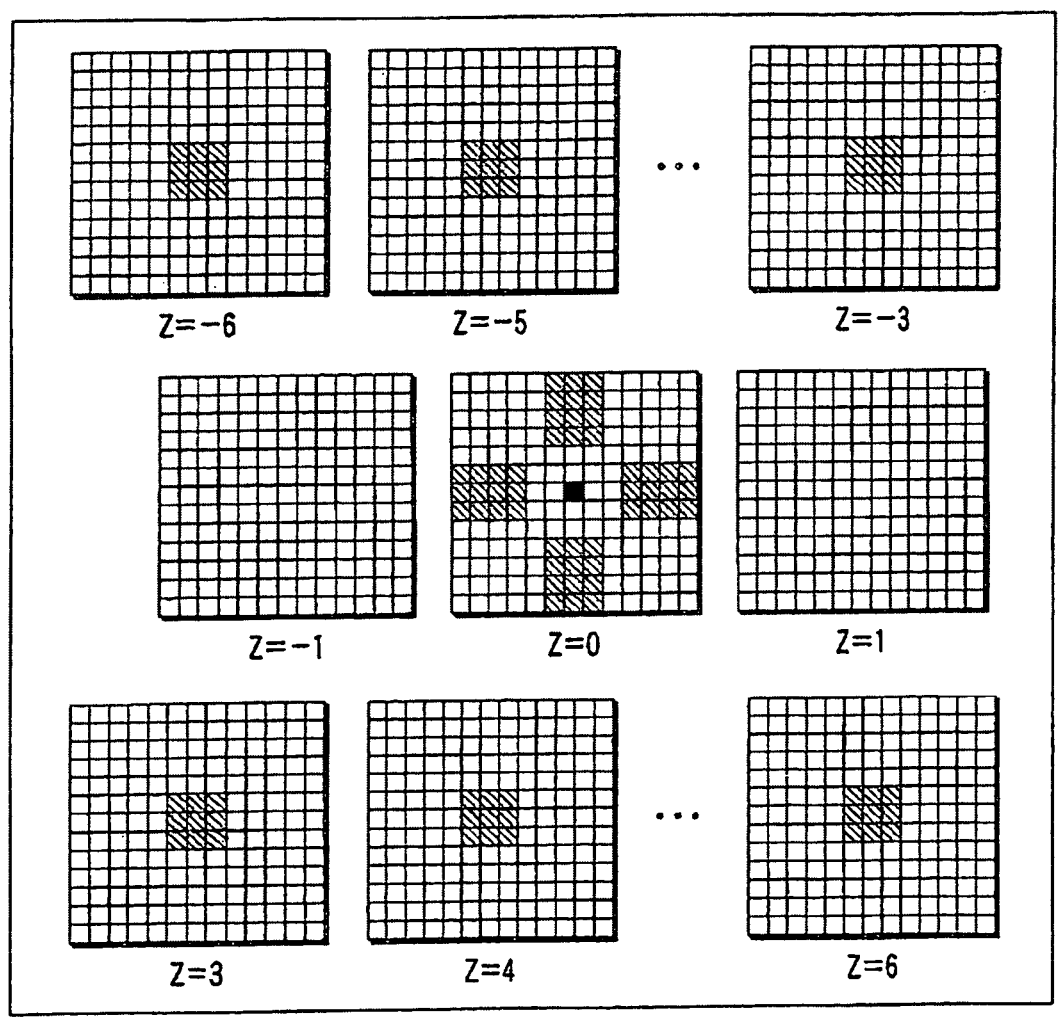
FIG. 2 is a diagram illustrating an example of volume data to be subjected to three-dimensional CFAR processing.
Figure 3:
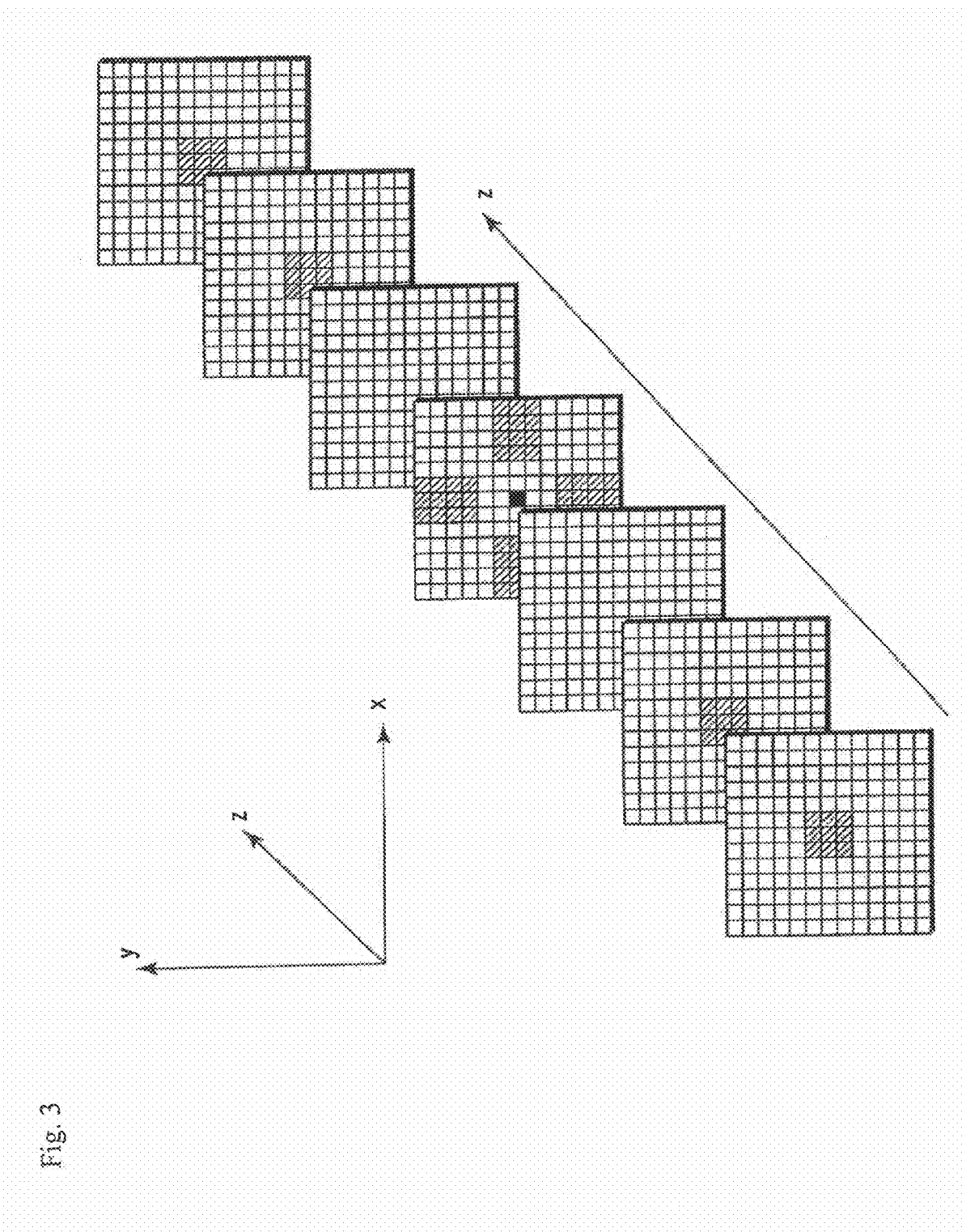
FIG. 3 is a diagram illustrating another example of the volume data to be subjected to the three-dimensional CFAR processing.

FIGS. 2 and 3 are diagrams illustrating examples of the volume data to be subjected to the CFAR processing according to this embodiment. In the volume data shown in FIGS. 2 and 3, six ultrasonic images are formed at both sides of the center (Z=0) in the Z-axis direction (a direction that is substantially orthogonal to the ultrasonic image, which is referred to as a depth direction). A white rectangle indicates a general pixel forming the ultrasonic image, a black rectangle indicates an interesting pixel Pi among the pixels forming the ultrasonic image. A rectangle of an intermediate color between white and black indicates a pixel (adjacent pixel) that is positioned adjacent to the interesting pixel Pi and used for an averaging process (1), which will be described below. The pattern of the adjacent pixels shown in FIGS. 2 and 3 is referred to as a 'kernel'. In addition, CFAR processing using the kernel that is three-dimensionally defined in this embodiment is referred to as 'three-dimensional CFAR processing'.

The CFAR processing according to this embodiment is performed by the following processes (1) to (3).

(1) First, the average value of the brightnesses of the adjacent pixels of each interesting pixel $P_i$ is calculated. In this case, the brightness of the interesting pixel $P_i$ may not be included in calculating the average value of the brightnesses of the adjacent pixels such that the brightness of the interesting pixel $P_i$ is not affected by the average value.

(2) Then, a value obtained by subtracting the average value from the pixel value of the interesting pixel $P_i$ is defined as a calculation result $K_i$ for the position of the interesting pixel $P_i$, and the value is stored in the internal storage unit 29. The calculation process is performed for all the interesting pixels $P_i$.

(3) Then, when a predetermined threshold value is T and $K_i \geq T$ is satisfied, the original brightness is used to display the interesting pixel $P_i$ (extraction of a microstructure). Meanwhile, when $K_i < T$, the brightness value of the interesting pixel $P_i$ becomes zero, and the interesting pixel is not displayed (removal). These processes are performed for all the interesting pixels $P_i$, thereby executing the CFAR processing on the images.

In the determination of (3), when $K_i \geq T$, the interesting pixel $P_i$ is displayed with a brightness of $K_i$. When $K_i < T$, the brightness value of the interesting pixel $P_i$ becomes zero, and the interesting pixel is not displayed (removal). In addition, it is possible to use an arbitrary pixel included in the two-dimensional image (image at Z=0 in FIGS. 2 and 3) from which a microstructure will be extracted as the interesting pixels $P_i$, by changing a value of i to a desired value.

Figure 4:
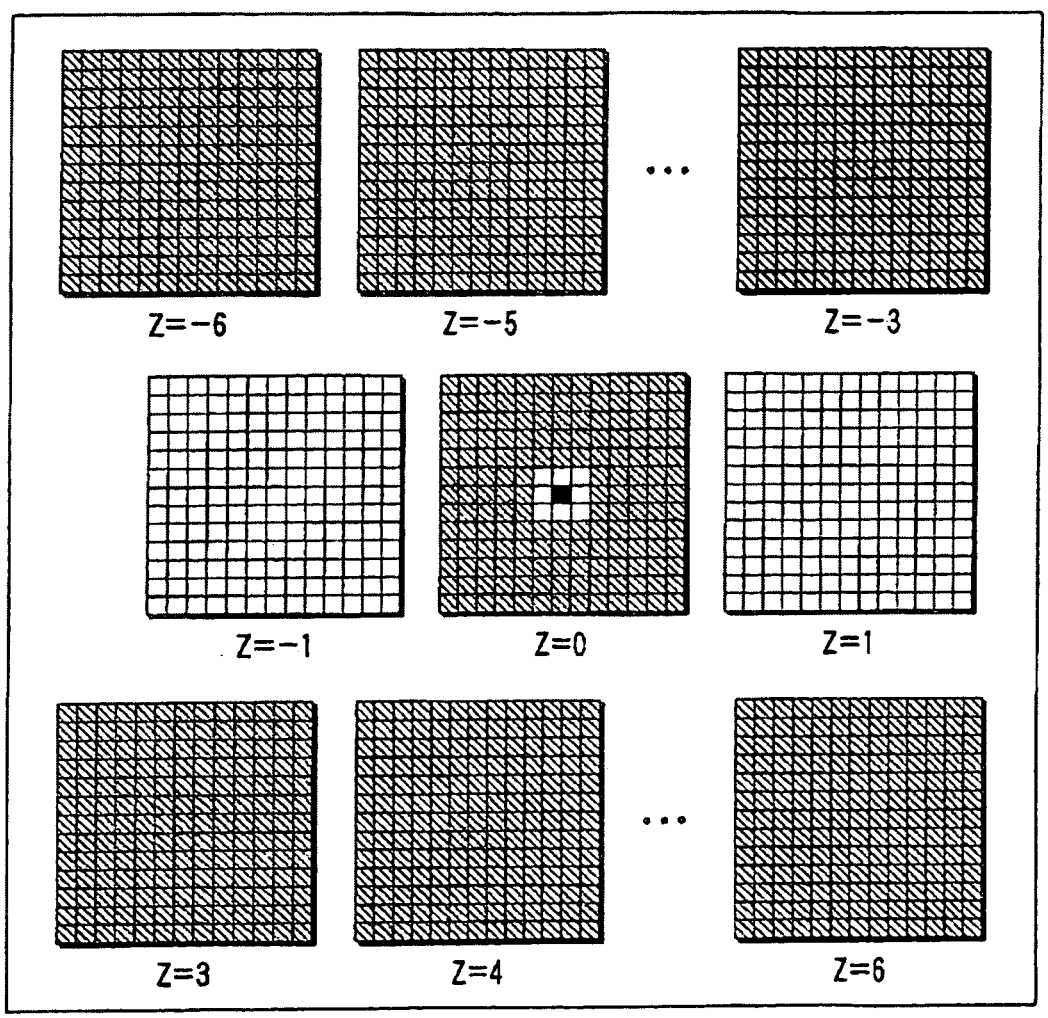
FIG. 4 is a diagram illustrating an example of a kernel pattern used in the three-dimensional CFAR processing.

In the example shown in FIGS. 2 and 3, the adjacent pixels are arranged in a cross shape in order to reduce the processing time. However, the arrangement of the adjacent pixels is not limited thereto. For example, the adjacent pixels may be arranged in a wide range as shown in FIG. 4 in order to calculate the average value when the processing time does not matter. In addition, in the process (1), the average value of the brightnesses is calculated, but the invention is not limited thereto. For example, the maximum brightness value may be calculated.

In the above-mentioned microstructure extracting process according to this embodiment, the pixel value of one interesting pixel $P_i$ is determined on the basis of the adjacent pixels of the interesting pixel $P_i$ in a direction (the depth direction, the Z-axis direction in FIGS. 2 and 3) orthogonal to the ultrasonic image as well as the adjacent pixels of the interesting pixel $P_i$ on the same ultrasonic image. In general, a continuous structure, such as the mammary gland, is distributed in a three-dimensional space including the depth direction, while a microstructure, such as a micro calcified portion, is distributed in only a local area. Therefore, it is possible to capture and select a high-brightness pixel having three-dimensional continuity by using a three-dimensional kernel pattern including the depth direction as well as the adjacent pixels on the same ultrasonic image.

Figure 5A:
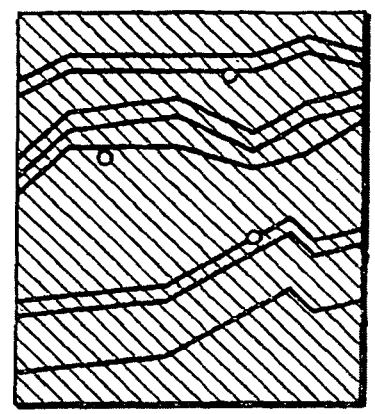
FIG. 5A is a diagram illustrating the effect of a microstructure extracting process according to the first embodiment.
Figure 5B:
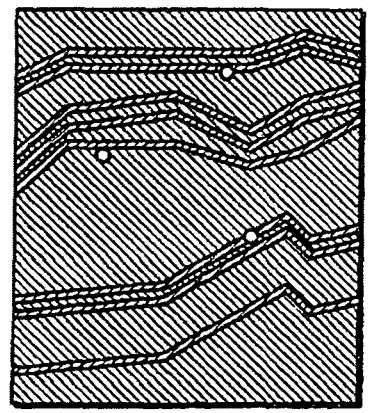
FIG. 5B is a diagram illustrating the effect of the microstructure extracting process according to the first embodiment.
Figure 5C:
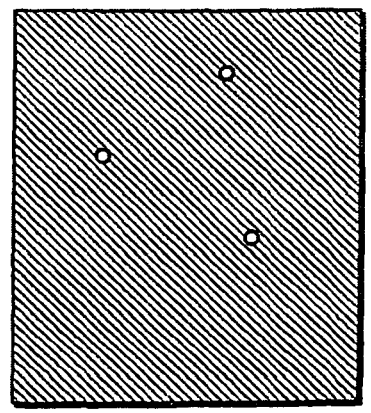
FIG. 5C is a diagram illustrating the effect of the microstructure extracting process according to the first embodiment.

FIGS. 5A, 5B, and 5C are diagrams illustrating the effects of the microstructure extracting process according to this embodiment. In the B-mode image shown in FIG. 5A (that is, an image before the microstructure extracting process according to this embodiment), a breast duct structure or a micro calcified portion is extracted, and the visibility thereof is too low to view it. The image shown in FIG. 5B is obtained by two-dimensional CFAR processing using the kernel that is two-dimensionally defined. In the image, a speckle pattern is reduced and a portion of the mammary gland other than the micro calcified portion also remains. Therefore, the visibility of the image is slightly lowered. The image (microstructure extracted image) shown in FIG. 5C is obtained by the microstructure extracting process according to this embodiment. In the microstructure extracted image, the micro calcified portion is extracted better than the images shown in FIGS. 5A and 5B. This is because the three-dimensional CFAR processing can selectively remove the mammary gland (continuous structure) having continuity in the depth direction.

The CFAR processing is effective to extract a signal having brightness that deviates from a speckle variation. A high pass filter (a signal process of extracting only a high frequency component) may be used to obtain the same effect as described above. A method using the high pass filter may be used instead of the CFAR processing, but the CFAR processing is more preferable to reduce the speckle pattern.

(Operation)

Figure 6:
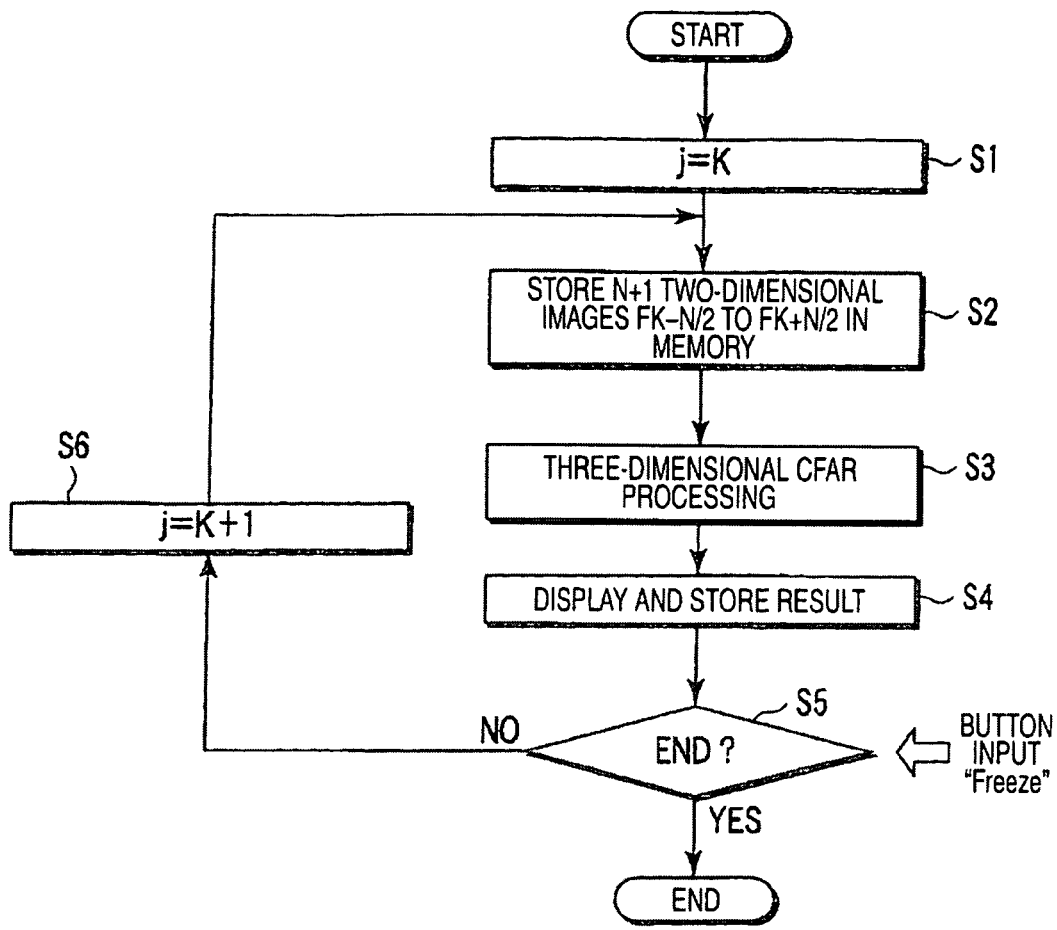
FIG. 6 is a flowchart illustrating the flow of the microstructure extracting process according to the first embodiment.

FIG. 6 is a flowchart illustrating the flow of the microstructure extracting process according to this embodiment. As shown in FIG. 6, first, the image generating unit 25 selects a frame (j=k) of tomographic images, which is a target, captures three-dimensional image data composed of N+1 frames $F_{k-N/2}$ to $F_{k+N/2}$ (in FIGS. 2 and 3, 13 frames up to Z=−6 to +6) including the frame, and stores the image data in a predetermined memory (Steps S1 and S2).

Then, the image generating unit 25 sets, as three-dimensional image data, a kernel including a predetermined three-dimensional pattern in which pixels included in the tomographic image, which is a target, are used as interesting pixels, and performs three-dimensional CFAR processing (Step S3). As such, in the microstructure extracting process according to this embodiment, CFAR processing is performed on a plurality of tomographic images, that is, the brightness of three-dimensional spatial information, and a microstructure extracted image is generated on the basis of a target tomographic image. The image synthesizing unit 27 displays the generated microstructure extracted image on the monitor 14, and the generated microstructure extracted image is automatically stored in the storage unit 29 (Step S4). The microstructure extracted image may be displayed in a dual display mode or a triplex display mode together with, for example, a B-mode image before the CFAR processing or a B-mode image after the CFAR processing. In this case, when different types of images are displayed at the same time, the cursor is arranged so as to correspond to the same position on each image.

Next, when the microstructure extracting process is further performed on another two-dimensional image $F_{k+1}$, the processes from Steps S1 to S4 are repeated (Step S5).

According to the above-mentioned structure, the following effects can be obtained.

According to the ultrasonic diagnostic apparatus of this embodiment, for example, in the diagnosis of the breast, the liver, and the pancreas, the filtering process performed on an ultrasonographic image (two-dimensional image) is three-dimensionally expanded, and removes a speckle pattern using the ultrasonographic image as well as information related to the direction (depth direction) that is substantially orthogonal to the ultrasonographic image. Therefore, it is possible to discriminate a continuous structure that is three-dimensionally distributed from a local microstructure and generate a microstructure extracted image from which a microstructure is extracted. For example, the doctor views the microstructure extracted image to find a microstructure, which is hardly discriminated from a speckle pattern by eyes and appears in only a specific tomographic image, in a short time.

Further, according to the ultrasonic diagnostic apparatus of this embodiment, it is possible to read from the storage unit a desired one of a B-mode image before a speckle pattern is removed, a B-mode image after a speckle pattern is removed, and a microstructure extracted image, and display the read image in a predetermined display mode, such as a dual display mode or a triplex display mode. In addition, when different types of images are displayed at the same time, the cursor is arranged so as to correspond to the same position on each image. Therefore, an observer, such as a doctor, can display a microstructure extracted image in a predetermined display mode and at a predetermined timing for the purpose of use, and specify and observe a microstructure rapidly and simply using plural kinds of images.

(Second Embodiment)

Next, a second embodiment of the invention will be described.

The structure of an ultrasonic diagnostic apparatus according to the second embodiment is substantially the same as that shown in FIG. 1. Hereinafter, only different functions from those in the first embodiment will be described.

An image generating unit 25 performs a process related to a microstructure extracting function (microstructure extracting process) according to this embodiment.

A control processor 28 reads from an internal storage unit 29 a dedicated program for implementing the microstructure extracting function according to this embodiment, expends the read program on its own memory, and performs predetermined arithmetic and control processes.

(Microstructure Extracting Function)

The microstructure extracting function according to this embodiment performs the microstructure extracting process using a process for removing a speckle pattern and a depth-direction arithmetic process for calculating spatial continuity in the depth direction.

Figure 7A:
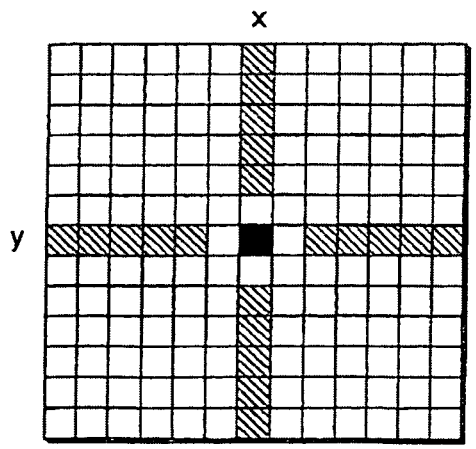
FIG. 7A is a diagram illustrating an example of a kernel pattern used in two-dimensional CFAR processing.
Figure 7B:
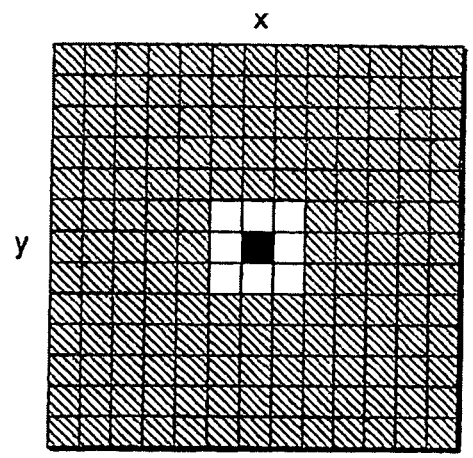
FIG. 7B is a diagram illustrating another example of the kernel pattern used in the two-dimensional CFAR processing.

That is, in the microstructure extracting function according to this embodiment, N tomographic frames are read, and then a process for removing a speckle pattern is performed on each of the frames. In this embodiment, for clarity of description, CFAR processing (two-dimensional CFAR processing) using a two-dimensional kernel that is defined on the same ultrasonic image, which is shown in FIGS. 7A and 7B, is performed as the process for removing a speckle pattern. However, the invention is not limited thereto. For example, a similarity filtering process or a spatial compounding process may be used instead of the two-dimensional CFAR processing.

Then, a depth-direction arithmetic process is performed on N frames of images from which a speckle pattern has been removed to generate a microstructure extracted image. The depth-direction arithmetic process is for determining the continuity of a structure (a high-brightness region) in the depth direction on the ultrasonic image. For example, the following method may be used as the depth-direction arithmetic process.

(1) Difference Operation

It is considered that a continuous structure remaining on the ultrasonic image after the two-dimensional CFAR processing is larger than a micro calcified portion and has continuity in the depth direction. From this viewpoint, it is assumed that the continuous structure exists (is imaged) in the state shown in FIG. 8 on each of the frames after the two-dimensional CFAR processing. Therefore, when a difference image is generated from continuous or adjacent frame images (for example, an image $F_{j-1}$ is subtracted from an image $F_j$), it is possible extract only discontinuous microstructures (for example, micro calcified portions) using the difference image.

Further, as the distance between tomographic images decreases, the difference between images decreases. Therefore, when the size of a microstructure is larger than the difference between the images, it is expected that no difference effect will be obtained. In order to solve the problem, the difference operation may be performed at n frame intervals (where n is a natural number) as well as on adjacent frames, if necessary. In addition, the size of the microstructure depends on an individual. Therefore, it is preferable that the operator operate the input device 13 to arbitrarily select the frames for generating the difference image (that is, the value of n).

When the ultrasonic probe 12 is configured to include a tiling circuit, information on the distance between a plurality of tomographic images that are automatically acquired is obtained at the same time. Therefore, a tomographic image that is separated by a predetermined distance (for example, an average distance of 2 mm) on the basis of the distance between the obtained tomographic images may be specified.

In this embodiment, the difference image processing and the CFAR processing may be reversed. That is, a difference image may be generated from continuous or adjacent frame images, and then the CFAR processing may be performed on the obtained two-dimensional image to remove an unnecessary tissue image, thereby extracting discontinuous microstructures.

(2) Spatial Frequency Analysis

Figure 8:
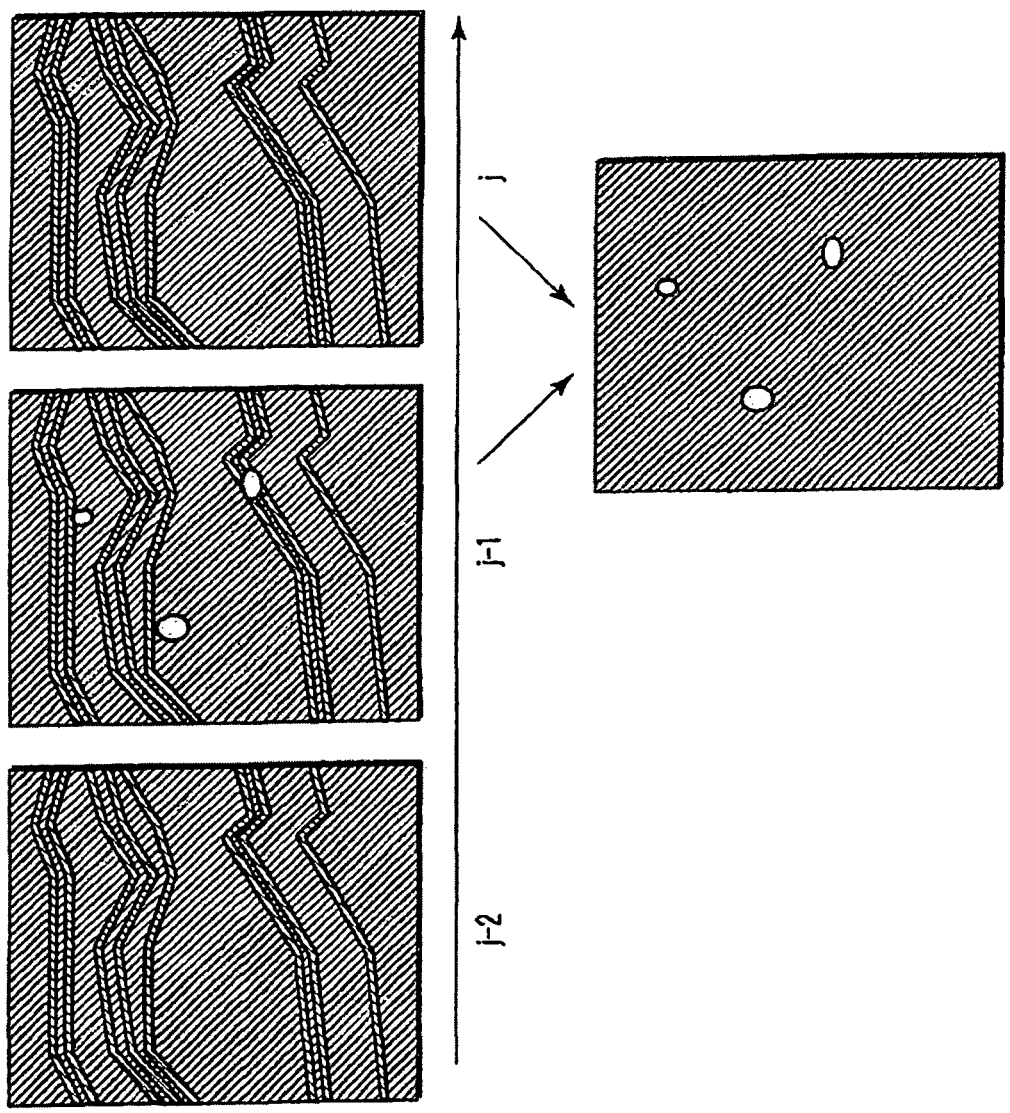
FIG. 8 is a diagram illustrating a depth-direction arithmetic process (difference process).
Figure 9:
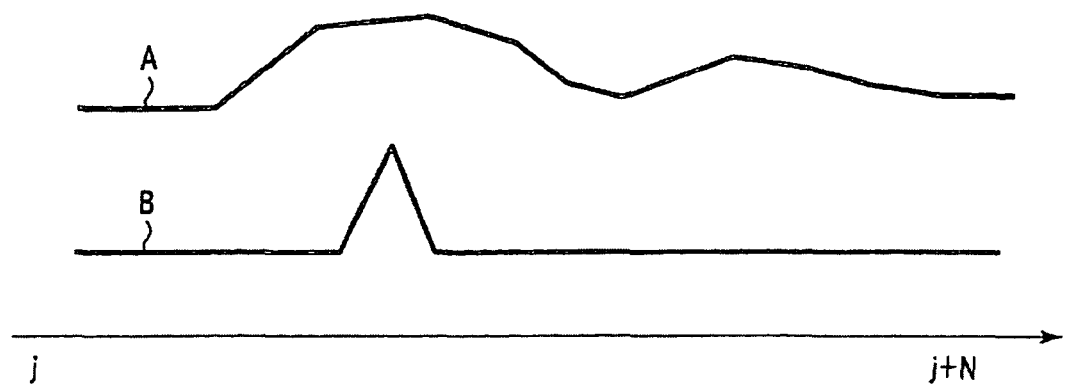
FIG. 9 is a diagram illustrating a depth-direction arithmetic process (frequency analyzing process).

FIG. 9 is a graph illustrating a frequency variation in the depth direction for pixels corresponding to the positions between the N pixels shown in FIG. 8. In FIG. 9, a graph A indicates that the frequency variation of the pixel values of the pixels that do not correspond to the microstructure in the depth direction is slow. Meanwhile, a graph B indicates that the frequency variation of the pixel values of the pixels that correspond to the microstructure in the depth direction is rapid. Therefore, when a high pass filter process is performed in the depth direction, the slow variation is removed. As a result, it is possible to extract only a microstructure, such as a micro calcified portion.

(First Modification)

Next, a modification of the microstructure extracting process according to this embodiment will be described.

In general, during three-dimensional scanning, when deviation occurs from the tomographic layer in the vertical and horizontal directions (in the x and y directions in FIGS. 2 and 3), the continuity of the pixels may be lost even in a continuous structure. Modification 1 provides a method for solving this problem.

That is, two-dimensional CFAR processing is performed on each two-dimensional image included in volume data, and image processing is performed to reproduce as a new image the maximum value of comparison between each pixel of each two-dimensional image before the depth-direction arithmetic process with adjacent pixels on the two-dimensional image. This image processing can represent a pixel value P(x, y) in a coordinate system (x, y) as follows:

$$P'(x,y)=MAX[P(x-i, y-j)],$$

(where i and j are arbitrary integers satisfying $-m \leq i \leq m$ and $-n \leq j \leq n$).

Even when deviation occurs in the horizontal and vertical directions, brightness information that remains in the two-dimensional CFAR processing can be included in each two-dimensional image by the image processing. Therefore, it is possible to preferably perform the difference operation and the frequency analysis method as the depth-direction arithmetic process.

(Modification 2)

Next, another modification of the microstructure extracting process according to this embodiment will be described. A second modification uses a method different from that of the first modification to correct the deviation between two-dimensional images in the horizontal and vertical directions.

That is, the second modification uses a motion vector between two two-dimensional images to correct the deviation between the two-dimensional images in the horizontal and vertical directions. For example, a technique for correcting image blur in the image frames that are continuous in the time axis direction (for example, a technique for dividing one image into a plurality of regions and calculating the movement direction and the displacement between the frames in each of the regions from the correlation between image patterns) has already been applied to video cameras on the market. When the motion vector that is calculated by this technique is used to correct the display positions of the image frames, image blur in the horizontal and vertical directions is reduced, and it is possible to ideally discriminate microstructures from the other structures.

(Operation)

Figure 10:
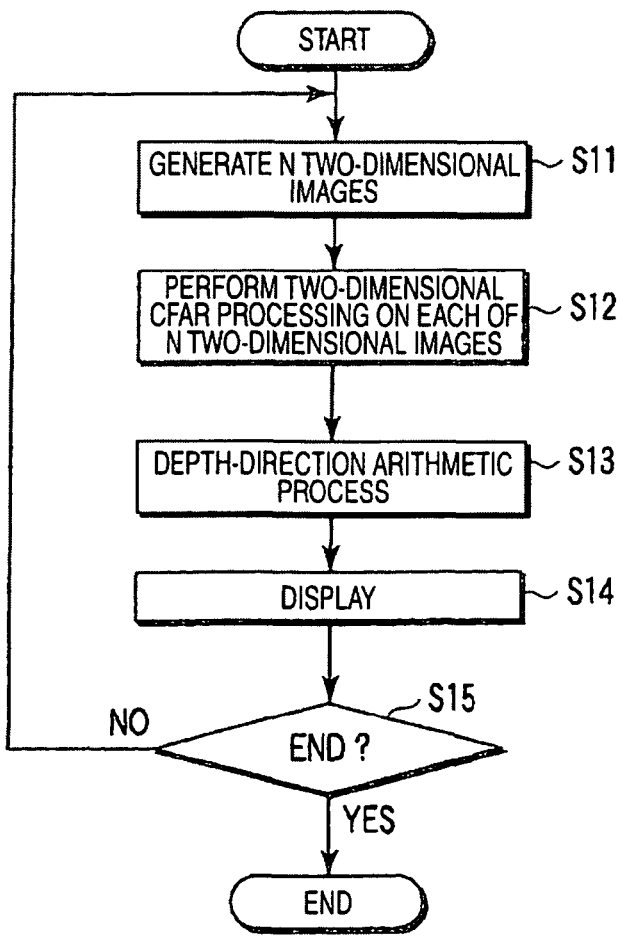
FIG. 10 is a flowchart illustrating the flow of a microstructure extracting process according to a second embodiment.

FIG. 10 is a flowchart illustrating the flow of the microstructure extracting process according to this embodiment. As shown in FIG. 10, first, the image generating unit 25 receives three-dimensional image data composed of N two-dimensional images, which are targets, and stores the image data in a predetermined memory (Step S11).

Then, the image generating unit 25 sets a kernel having a predetermined two-dimensional pattern to each of the two-dimensional images, and performs two-dimensional CFAR processing (Step S12). Then, the image generating unit 25 uses each of the two-dimensional images to perform the depth-direction arithmetic process, thereby generating a microstructure extracted image (Step S13). The generated microstructure extracted image is displayed on the monitor 14 by the image synthesizing unit 27 and is automatically stored in, for example, the internal storage unit 29 (Step S14).

According to the ultrasonic diagnostic apparatus of the above-described embodiment, a process of removing a speckle pattern from each of the two-dimensional images is performed, and then the depth-direction arithmetic process is performed. Therefore, it is possible to extract a high-brightness region from the two-dimensional image, extract a microstructure on the basis of the distribution of the high-brightness regions in the depth direction, and form a microstructure extracted image using the extracted microstructure. As a result, it is possible to obtain the same effects as those in the first embodiment.

(Third Embodiment)

Next, a third embodiment of the invention will be described. The third embodiment differs from the second embodiment in that the process of removing a speckle pattern is not performed, but the depth-direction arithmetic process is directly performed using N two-dimensional images.

Figure 11:
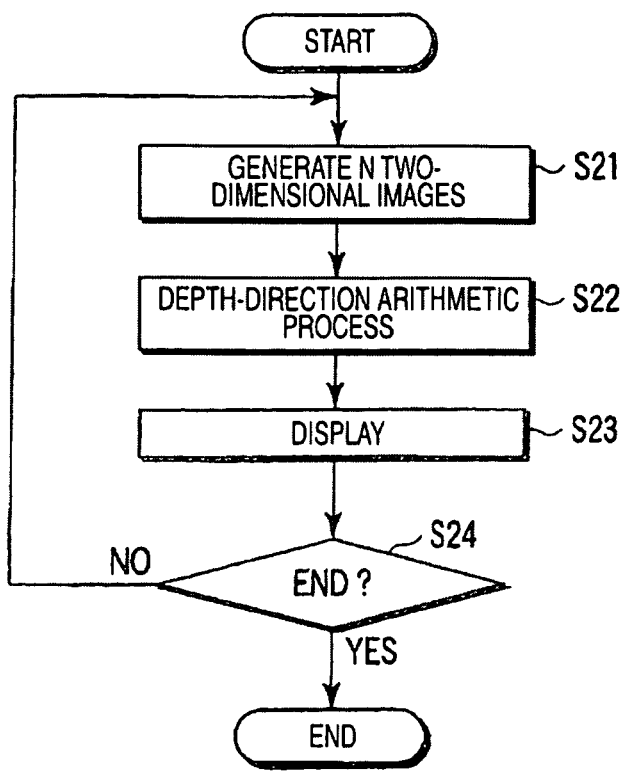
FIG. 11 is a flowchart illustrating the flow of a microstructure extracting process according to a third embodiment.

FIG. 11 is a flowchart illustrating the flow of a microstructure extracting process according to this embodiment. As shown in FIG. 11, first, the image generating unit 25 receives three-dimensional image data composed of N two-dimensional images, which are targets, and stores the image data in a predetermined memory (Step S21).

Then, the image generating unit 25 uses each of the two-dimensional images to perform the depth-direction arithmetic process, thereby generating a microstructure extracted image (Step S22). The generated microstructure extracted image is displayed on the monitor 14 by the image synthesizing unit 27 and is automatically stored in, for example, the internal storage unit 29 (Step S13).

According to the ultrasonic diagnostic apparatus of the above-described embodiment, the depth-direction arithmetic process is performed using a plurality of two-dimensional images forming three-dimensional image data. Therefore, it is possible to extract microstructures on the basis of the distribution of structures included in the three-dimensional image data in the depth direction, and form a microstructure extracted image using the extracted microstructures. As a result, it is possible to obtain the same operations and effects as those in the first and second embodiments.

(Fourth Embodiment)

Next, a fourth embodiment of the invention will be described. An ultrasonic diagnostic apparatus 1 according to this embodiment is provided with a position detecting device 15, if necessary. The position detecting device detects information on the position of the ultrasonic probe 12 with respect to an object to be captured (that is, a diagnosis part). Examples of the information on the position of the ultrasonic probe 12 include absolute positional information of the ultrasonic probe 12, relative positional information thereof, positional information of the ultrasonic probe 12 before operation, and information for specifying the operating speed, the operating time, and the position of the ultrasonic probe 12 during scanning.

Figure 12:
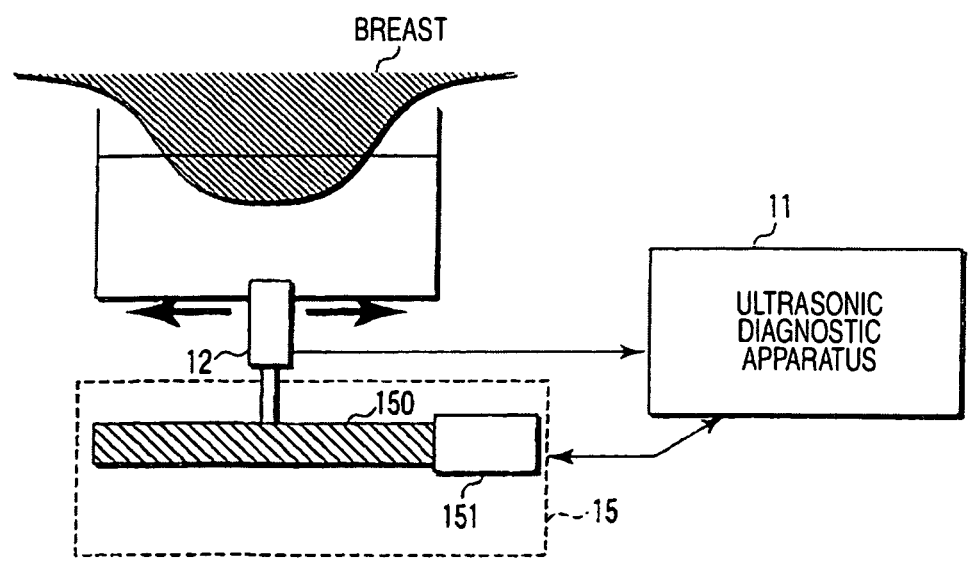
FIG. 12 is a diagram illustrating an example of a position detecting device 15.

FIG. 12 is a diagram illustrating an example of the position detecting device 15. As shown in FIG. 12, the position detecting device 15 includes a movable stage 150 and a driving unit 151. The ultrasonic probe 12 may be provided on the movable stage 150 with a dedicated adapter interposed therebetween. The driving unit 151 moves the ultrasonic probe 12 along the movable stage 150 under the control of the control processor 28. In addition, the driving unit 151 has a rotary encoder provided therein, detects the position of the ultrasonic probe 12 on the movable stage 150, and sequentially transmits the detected results to the control processor 28.

When an ultrasonic image is captured, the breast, which is a diagnosis target, is disposed at a predetermined position in a water tank 17, and is fixed so as not to be moved during examination. In addition, the ultrasonic probe 12 and the position detecting device 15 are arranged on the bottom of the water tank 17. The control processor 28 transmits or receives ultrasonic waves while controlling the driving unit 151 such that the ultrasonic probe 12 is moved at a predetermined speed, thereby performing self-propelled ultrasonic scanning. The image from the ultrasonic probe 12 is transmitted to the ultrasonic diagnostic apparatus, similar to the first embodiment. Further, positional information acquired by the driving unit 151 is used to generate information on the position of the ultrasonic probe, which will be described below, in real time, and is stored and managed as incidental information of each frame.

(Microstructure Extracting Function)

When a spot that is considered as a microstructure (hereinafter, simply referred to as a spot) is observed from an ultrasonographic image (a B-mode image), actually, it is difficult to determine whether the spot is a structure, such as a micro calcified portion, or a portion of a tissue structure, such as the mammary gland. In particular, it is difficult to determine the type of structures in one still picture.

However, the two structures are different from each other in the following.

A. The composition of a micro calcified substance is harder than that of a biological tissue, and theoretically, the intensity of an ultrasonic signal reflected from the micro calcified substance may be higher than that of the biological tissue. The inventor's studies proved that the signal level of a spot by micro-calcification was slightly higher than the maximum value of a surrounding speckle pattern. However, when the signal level is displayed on the monitor as brightness, it is difficult to determine the difference between the signal levels with eyes.

B. A micro calcified substance is a microstructure that exists locally, but a biological tissue, such as the mammary gland, is a continuous structure that is three-dimensionally arranged in a predetermined range. In addition, essentially, there is a great difference between the micro calcified substance and the biological tissue in spatial distribution. Therefore, it is expected to determine the difference between the two substances considering three-dimensional continuity in the depth direction.

Therefore, the invention has been made paying attention to this viewpoint, and discriminates the two substances, on the basis of a very small difference in brightness and the shape of spatial distribution, to generate an image from which microstructures are certainly removed (microstructure extracted image), in the diagnosis of, for example, the mammary gland, the liver, and the pancreas.

Further, a process (microstructure extracting process) using the microstructure extracting function according to this embodiment is performed on image group data. The term 'image group data' means volume data having a plurality of two-dimensional images or data composed of a plurality of different two-dimensional images (which does not necessarily form complete volume data). In this embodiment, for clarity of description, a microstructure extracting process using the image group data as volume data will be described. The image group data can be obtained by mechanically tilting the ultrasonic probe 12 in a direction orthogonal to the direction in which vibrators are arranged to scan a three-dimensional region with ultrasonic waves. Alternatively, the image group data can be obtained by electrically controlling the ultrasonic probe 12 having ultrasonic vibrators two-dimensionally arranged to scan a three-dimensional region with ultrasonic waves. In this case, it is also possible to obtain the same effects as described above. Further, the image group data can be obtained by manually acquiring a plurality of tomographic images using a self-propelled scanning device shown in FIG. 12 or an ultrasonic probe (which may be provided with a position sensor, if necessary) having ultrasonic vibrators one-dimensionally arranged.

Figure 13:
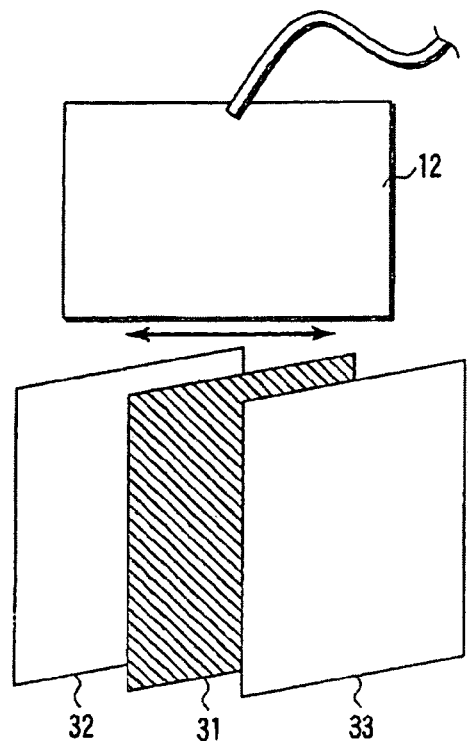
FIG. 13 is a diagram illustrating the microstructure extracting process.

FIG. 13 is a diagram illustrating the microstructure extracting process. As shown in FIG. 13, a target image 31 and a reference image 32 are selected from a plurality of two-dimensional images included in image part data. The target image 31 is an image to be subjected to the microstructure extracting process according to this embodiment. The reference image 32 is a separate tomographic image (for example, an image that is separated from the target image by k frames) that is different from the target image 31 in space. It is preferable that these images be tomographic images in the vertical direction from the ultrasonic probe, similar to the B-mode diagnosis.

Figure 14A:
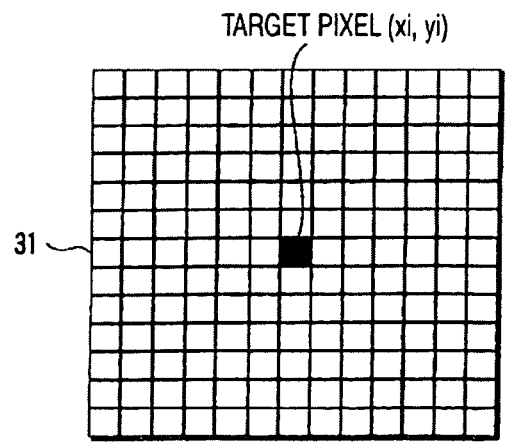
FIG. 14A is a schematic diagram illustrating a target image.
Figure 14B:
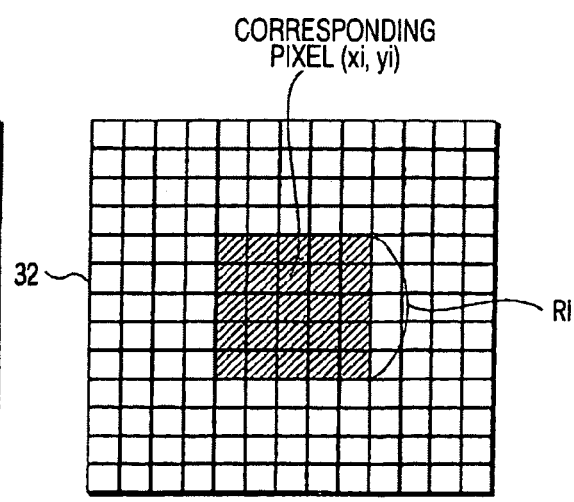
FIG. 14B is a schematic diagram illustrating a reference image.

FIG. 14A is a diagram schematically illustrating the target image, and FIG. 14B is a diagram schematically illustrating the reference image. The microstructure extracting process according to this embodiment subtracts the reference image from the target image to generate a difference image. In this case, the representative value of a pixel in a reference region $R_i$ of the reference image with respect to each pixel $(x_i, y_i)$ (which is called a target pixel or an interesting pixel) of the target image is determined, and this value is subtracted from the value of the target pixel (xi, yi). The reference region has an arbitrary size and is set on the reference image so as to include a pixel (corresponding pixel) whose coordinates on the reference image are the same as those on the target pixel. The reference region Ri may have any representative value as long as the value can represent the characteristics of the reference region Ri. Specifically, a maximum value, an average value, or an intermediate value may be used as the representative value. In this embodiment, the maximum value is used as the representative value. The generation of the difference image can be represented by Equation (1) given below:

$$Qi(xi,yi)=Pi(xi,yi)-\text{MAX}[P_{i-k}(xi+m,yi+n)] \quad (1),$$

(where Qi(xi, yi) indicates the value of each pixel of the difference image, Pi(xi, yi) indicates the value of the target pixel of the target image, $P_{i-k}$(xi, yi) indicates the value of each pixel in the reference image that is disposed at a position spatially corresponding to Pi(xi, yi), $P_{i-k}$(xi+m, yi+n) indicates the value of each pixel in the reference region Ri, m and n are arbitrary values designating the size of the reference region, and MAX[ ] indicates an operation for selecting the maximum value within [ ]). Therefore, FIG. 14B shows the reference region Ri composed of ±2 pixels in both the x-axis direction and the y-axis direction, a total of 25 pixels. In this arithmetic process, it is preferable that, when the result has a negative value, all pixels have a value of 0 (brightness is black).

Figure 15:
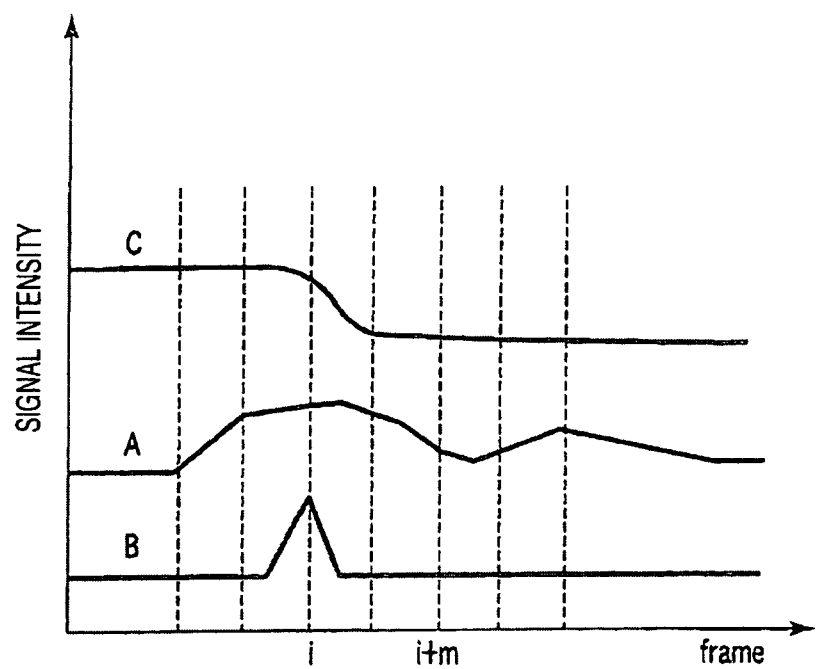
FIG. 15 is a diagram illustrating an example of a variation in the signal intensity (brightness of an image) of each pixel.

The difference image generated by the microstructure extracting process according to this embodiment is formed by removing a continuous structure and a random speckle pattern and appropriately imaging microstructures. The reason is as follows. That is, it is considered that the continuous structure remaining on the two-dimensional ultrasonic image forming the image group data is larger than a micro calcified substance and has continuity in the depth method. From this viewpoint, when paying attention to one point on the ultrasonographic image, it is expected that the signal intensity (the brightness of an image) A of a continuous structure will vary slowly as shown in FIG. 15. Meanwhile, it is expected that a microstructure will be included in only a specific image as shown as a signal intensity line B in FIG. 15. Therefore, when the difference image is generated from a continuous or adjacent frame image (for example, an image $F_{i-1}$ (reference image) is subtracted from an image $F_i$ (target image)), only a discontinuous microstructure (for example, a micro calcified portion) may be extracted from the difference image.

However, the inventors found that the difference image between the images was insufficient to effectively extract a microstructure. For example, when a random speckle pattern is formed on the target image, and when spatial positional deviation occurs between the target image and the reference image, it is difficult to perform effective extraction.

In the microstructure extracting process according to this embodiment, the difference image, serving as a microstructure extracted image, is generated by subtracting the maximum value of the pixel in the reference region Ri that is set on the reference image from the value of each pixel (xi, yi) of the target image. Therefore, for example, even when spatial positional deviation occurs between the target image and the reference image, a portion represented by the target pixel of the target image exists in the reference region of the reference image. As a result, it is possible to improve the extraction performance of a microstructure.

The microstructure extracting process according to this embodiment is not limited to the selection of a reference image and the selection of a reference region size. For example, the microstructure extracting process can be performed according to the following standards.

First, it is possible to select a target image on the basis of the size of an imaging target (in this case, a calcified portion). That is, when the difference operation is performed to reduce the distance between frames, the difference between images is reduced. Therefore, when the size of a microstructure is larger than the difference between the images, it is expected that no difference effect will be obtained. In order to solve this problem, it is preferable to select a frame that is sufficiently distant from the target image to be larger than the estimated size of a microstructure as the reference image.

Second, it is possible to select the size of the reference region on the basis of the degree of the positional deviation expected between the target image and the reference image. That is, when the difference operation is performed and the degree of the positional deviation between the target image and the reference image is larger than the size of the reference region, a portion represented by the target pixel of the target image does not exist in the reference region of the reference image. In order to solve this problem, it is preferable that the size of the reference region be larger than the degree of the positional deviation expected between the target image and the reference image.

Third, it is possible to select the reference image on the basis of the size of the speckle pattern. That is, when the difference operation is performed and the gap between the target image and the reference image is larger than the size of the speckle pattern, no difference effect is obtained, and the speckle pattern is extracted together with a microstructure. In order to solve this problem, it is preferable to select the reference image such that the gap between the target image and the reference image is smaller than the size of the speckle pattern. The size of the speckle pattern depends on the frequency of a transmitted ultrasonic wave. Therefore, it is preferable to select the reference image depending on the frequency of a transmitted ultrasonic wave.

Fourth, it is possible to select the size of the reference region and the reference image on the basis of the size of a structure other than an imaging target. That is, when the difference operation is performed and the gap between the target image and the reference image is larger than the size of a structure other than an imaging target, no difference effect is obtained, and the structure is extracted together with the imaging target. In order to solve this problem, it is preferable to select the reference image such that the gap between the target image and the reference image is smaller than the size of a structure other than the imaging target.

It is possible to manually operate the input device 13 to set the position of the reference image and the size of the reference region to arbitrary values on the basis of the above-mentioned standards. In addition, it is possible to determine the position of the reference image by controlling a tilting or scanning speed in the depth direction of the ultrasonographic image. In this embodiment, for clarity of description, both the gap between the target image and the reference image and the size of the reference region are several millimeters.

The position of the reference image can also be automatically determined by the following method. That is, first, the image generating unit 25 selects a frame $F_{i-1}$ as the reference image, and performs a difference operation between the selected frame and the target image $F_i$. Then, the image generating unit 25 calculates the total sum S1 of the brightness values (pixel value) of the difference image obtained by the difference operation. The same process is performed using the other frames $F_{i-2}, F_{i-3}, \ldots, F_{i-N}$ as the reference images, to calculate the total sums S2, S3, . . . , Si. In general, a large number of microstructures do not exist in the diagnosis image. Therefore, each of the total sum Si is a residue due to a very small variation in the tissue structure. As the distance between the frames increases, the total sum increases. From this viewpoint, it is possible to select a frame corresponding to the total sum si that is larger than a predetermined threshold value as a reference image suitable for the difference operation.

When the brightness value of a certain pixel varies like the signal intensity line B shown in FIG. 15, it is possible to appropriately discriminate a microstructure from a continuous structure and a random speckle pattern even though one reference image is used with respect to the target image. However, when the brightness value of a certain pixel varies like the signal intensity line C shown in FIG. 15, it is difficult to appropriately discriminate a microstructure from a continuous structure and a random speckle pattern using one reference image 32. The reason is that, when a variation in brightness is represented by the signal intensity line C shown in FIG. 15, the difference between the target image $F_i$ and a reference image $F_{i+m}$ does not become zero even in a microstructure.

Figure 16:
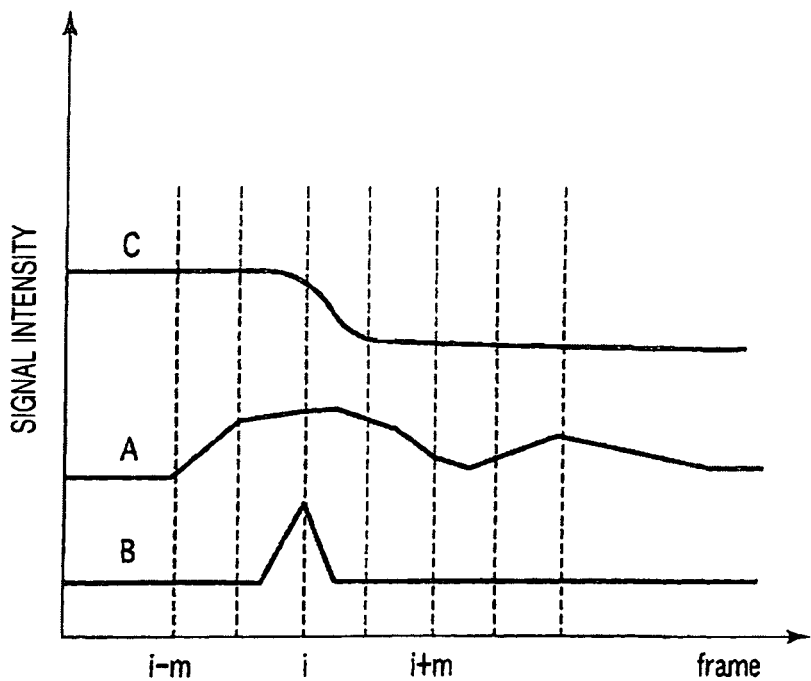
FIG. 16 is a diagram illustrating another example of the variation in the signal intensity (brightness of an image) of each pixel.

In order to solve this problem, the ultrasonic diagnostic apparatus 1 according to this embodiment can set two or more reference images 32. For example, as shown in FIG. 16, two reference images that are separated from the target image by ±m frames in the forward and backward directions are used to calculate the difference between the target image $F_i$ and the reference image $F_{i+m}$ and the difference between the target image $F_i$ and a reference image $F_{i-m}$. As a result, when the differences are not equal to each other, it is possible to assume that the variation in brightness is represented by the signal intensity line C in FIG. 15. Therefore, one of the differences having a small value is used as a value for the corresponding pixel of the difference image. Even when two or more reference images 32 are used, each reference image is selected by the above-mentioned standards. In addition, it is preferable that the reference images be selected so as to be symmetric with the target image, in order to more appropriately extract a microstructure.

DISPLAY EXAMPLES OF DIFFERENCE IMAGE

Next, display examples of the microstructure extracted image obtained by the microstructure extracting process will be described. The following display examples may be independently used, or they may be combined with each other.

Example 1

Figure 17A:
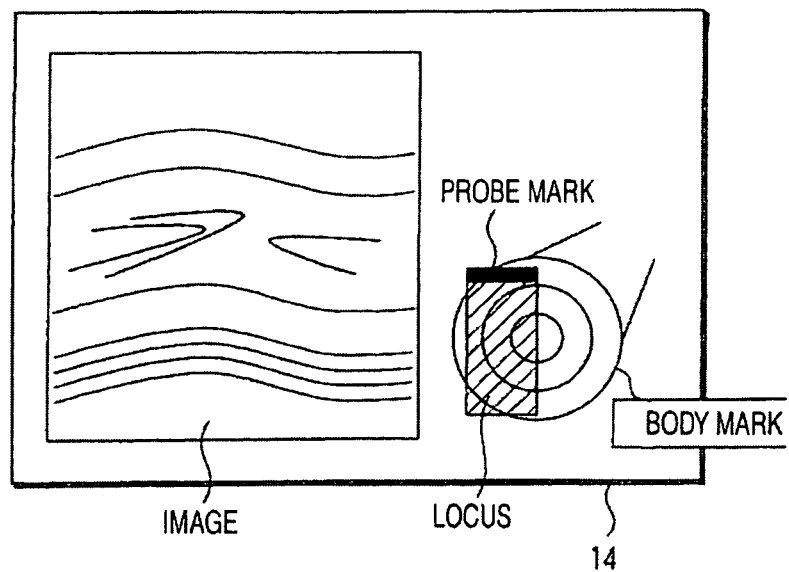
FIG. 17A is a diagram illustrating an example of the display of a microstructure extracted image.

In a display form according to this example, the difference image, serving as a microstructure extracted image, is displayed together with information on the position of the ultrasonic probe when the target image used to generate the difference image is acquired. Any information may be used as the information on the position of the ultrasonic probe as long as it can attain its purpose. For example, a schematic diagram of the ultrasonic probe 12 set on the body mark shown in FIG. 17A may be exemplified. The information on the position of the ultrasonic probe may be generated on the basis of, for example, the positional information of the ultrasonic probe detected by the position detecting device 16 shown in FIG. 12. In the case of the body mark shown in FIG. 17A, the image synthesizing unit 27 generates the body mark indicating the position of the ultrasonic probe, synthesizes the body mark with the difference image, and transmits the synthesized image to the monitor 14, under the control of the control processor 28. In this way, it is possible to display the difference image together with information indicating the position of the ultrasonic probe, as shown in FIG. 17A. In addition, the scanning range of the ultrasonic probe 12 or the region that has already been displayed may be displayed as a 'locus' in different colors on the body mark, on the basis of the positional information of the ultrasonic probe for all the two-dimensional images forming the image group data.

Example 2

Figure 17B:
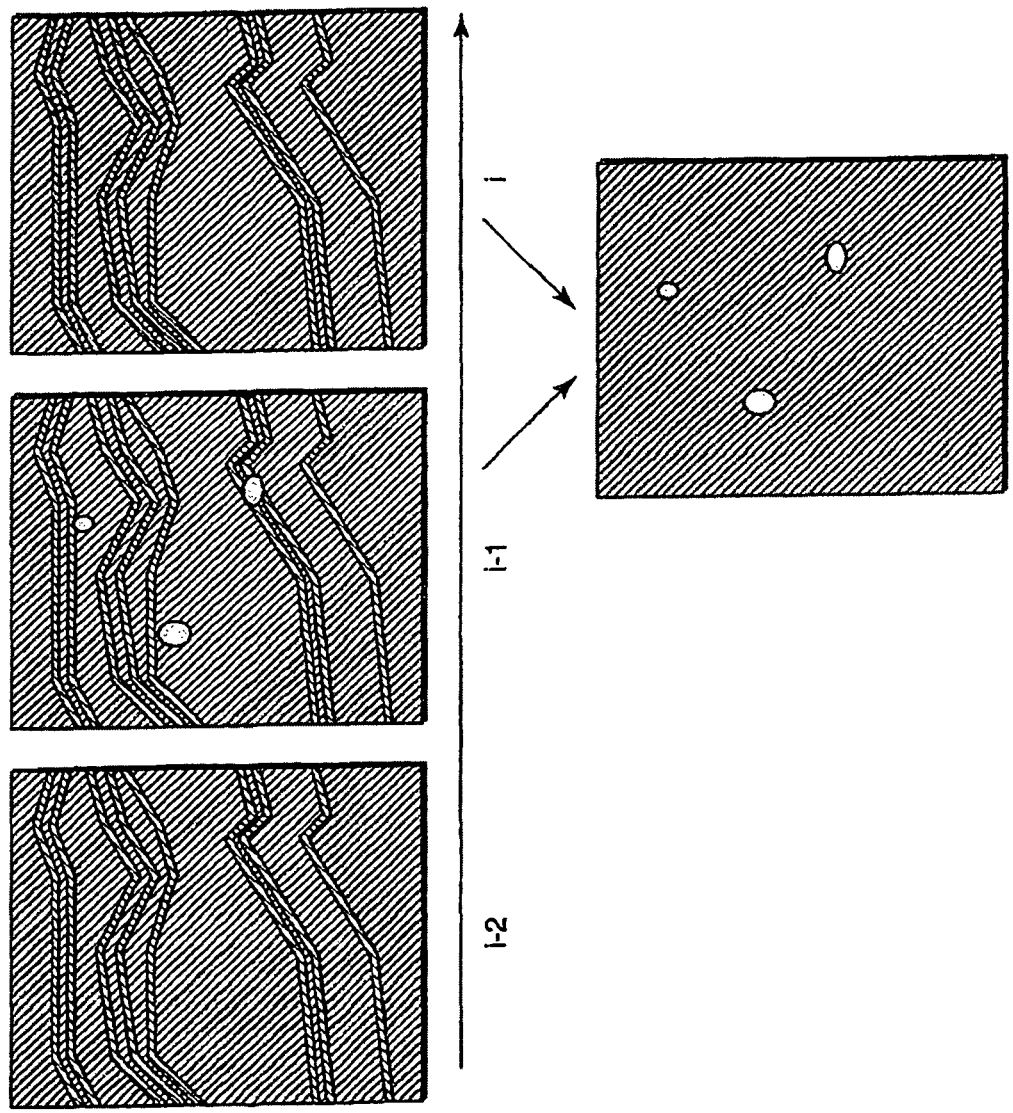
FIG. 17B is a diagram illustrating a microstructure extracted image using a difference image.

In a display form according to Example 2, as shown in FIG. 17B, an MIP (maximum intensity projection) process is performed using a plurality of difference images (for example, difference images corresponding to image group data) obtained by the microstructure extracting process, and an MIP image obtained by the MIP process is displayed as the microstructure extracted image. In this way, information of the microstructures included in the plurality of difference images can be condensed into one MIP image. It is possible to reduce the MIP image to a management data size by using the MIP image as attached data such as an electronic clinical chart.

Example 3

In a display form according to Example 3, quantitative analysis is performed to extract a difference image having predetermined reliability from image group data, and the MIP process according to Example 2 is performed using the difference image. That is, a brightness curve is generated for each pixel of a difference image corresponding to the image group data, and the brightness curve is used to calculate a variation over time and a standard deviation thereof during a certain period (for example, a frame interval). Among the obtained result, a pixel corresponding to a standard deviation having a remarkably different value (for example, a standard deviation that is larger than a predetermined threshold value) is more likely to be a microstructure. Therefore, it is possible to improve the extraction accuracy of a microstructure by extracting a difference image having the image and performing the MIP process using the difference image.

Example 4

In a display form according to Example 4, a B-mode image before the microstructure extracting process, a microstructure extracted image, and the MIP image obtained by the MIP process using the difference image can be displayed in any one of an overlap display mode, a dual display mode, and a triplex display mode. In the overlap display mode, a B-mode image before the speckle pattern is removed and a new image after the speckle pattern is removed can be discriminated from each other by changing their basic colors and overlapping the images with different colors. In a parallel display mode, such as the dual display mode, in each display mode that displays different types of images at the same time, a cursor is arranged so as to correspond to the same position on each image. Therefore, an observer, such as a doctor, can display a microstructure extracted image in a desired display mode and at a predetermined timing for the purpose of use, and specify and observe a microstructure rapidly and simply using plural kinds of images.

(Operation)

Figure 18:
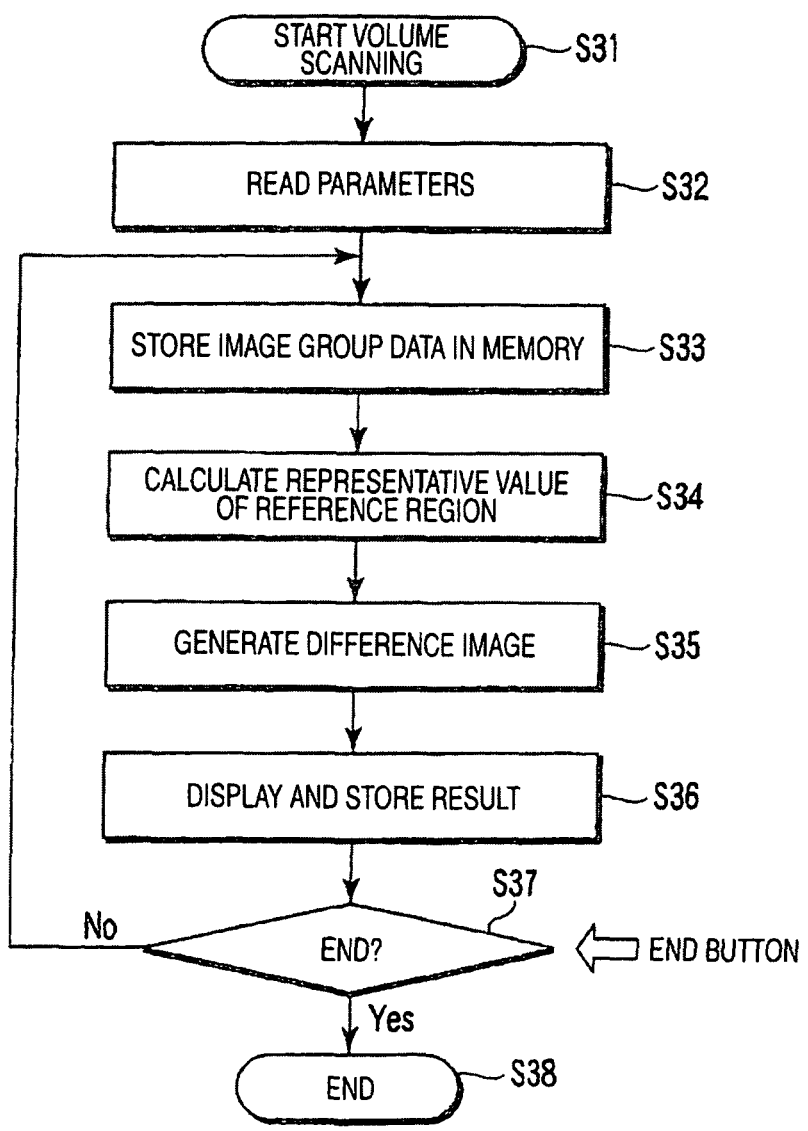
FIG. 18 is a flowchart illustrating the flow of a microstructure extracting process according to a first embodiment.

FIG. 18 is a flowchart illustrating the flow of the microstructure extracting process according to this embodiment. For clarity of description, it is assumed that the display form according to Example 1 is used in FIG. 18. As shown in FIG. 18, first, when volume scanning starts, an instruction to change to the microstructure extracting process is issued and a necessary parameter group is read (Steps S31 and S32). The parameter group required for the microstructure extracting process includes, for example, the number of reference images, a distance between the reference image and the target image, and the range of a smoothing process (maximum value operation).

Then, image group data related to the breast is acquired by volume scanning using a predetermined method, and is then stored in a memory (Step S33). Then, the image generating unit 25 calculates the representative value of the reference region of each reference image (Step S34). The microstructure extracting process is performed using the representative value to generate a plurality of difference images corresponding to the image group data (Step S35). The obtained difference images are displayed on the monitor 14 together with, for example, the body mark having the positional information of the ultrasonic probe, and are also automatically stored (Step S36).

Thereafter, the diagnostic apparatus repeatedly performs the microstructure extracting process until an instruction to end an image freeze mode or an image mode according to this embodiment is issued.

(Effects)

According to the above-mentioned structure, the following effects can be obtained.

According to the ultrasonic diagnostic apparatus of this embodiment, in the diagnosis of the breast, the liver, and the pancreas, a discontinuous microstructure is extracted using information on the direction (depth direction) that is substantially orthogonal to the image. In particular, a maximum value smoothing process of the microstructure extracting process can effectively remove residues due to a variation in the speckle pattern or the positional deviation of a structure in a cross-sectional direction, which are not removed by only the difference between the target image and the reference image.

Figure 17C:
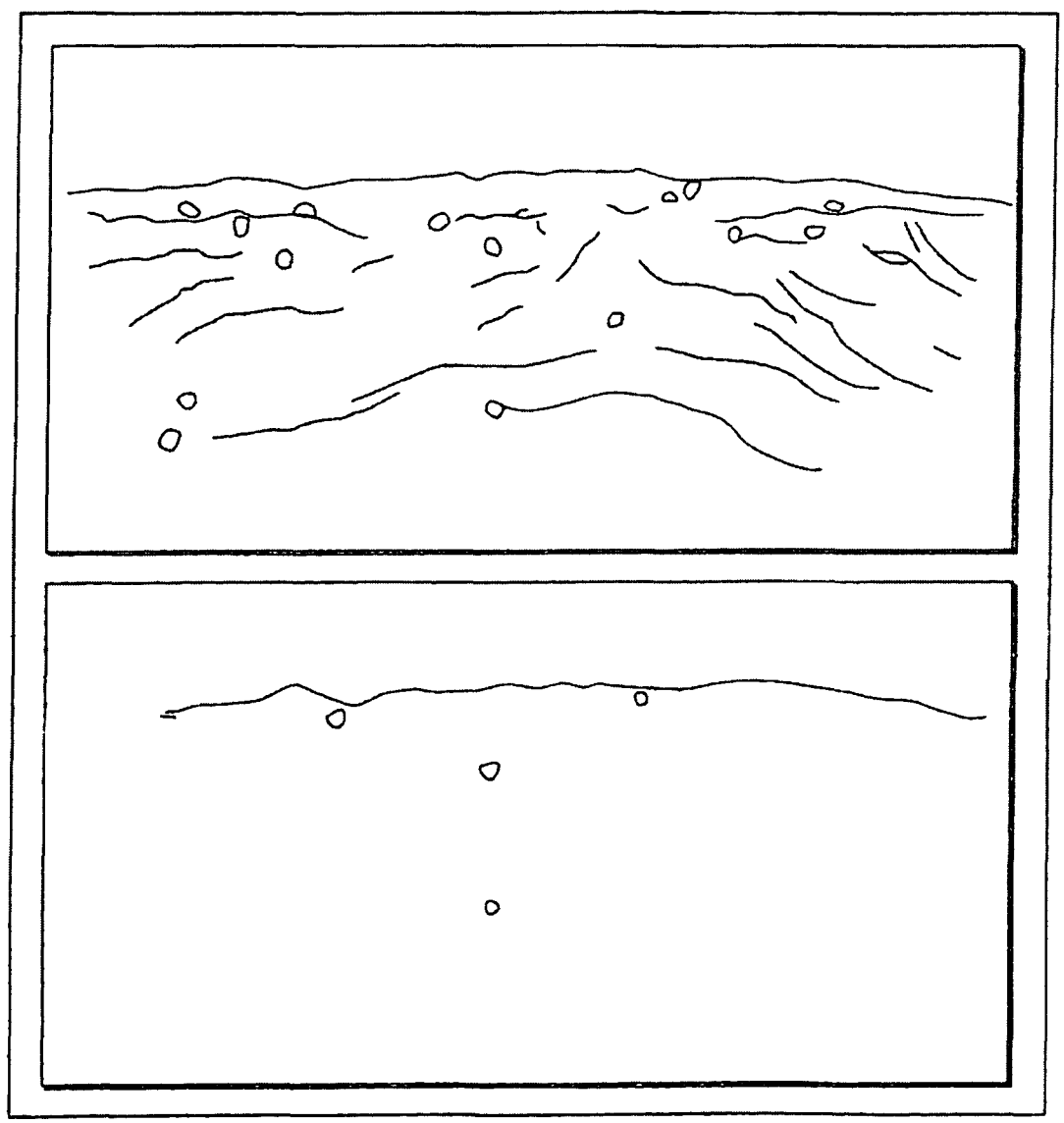
FIG. 17C is a diagram illustrating a B-mode image and a microstructure extracted image, in which an upper part shows the B-mode image and a lower part shows the microstructure extracted image.

An upper part of FIG. 17C shows a general B-mode image, and a lower part of FIG. 17C shows a microstructure extracted image. As can be seen from the comparison therebetween, a portion of tissue as well as a micro calcified portion is shown in the general B-mode image shown in the upper part of FIG. 17C, and there are a large number of high-brightness spots in the general B-mode image. Therefore, it is difficult to discriminate the micro calcified portions from the other portions with eyes. Meanwhile, micro calcified portions are extracted, and shown as high-brightness spots in the microstructure extracted image shown in the lower part of FIG. 17C.

Therefore, it is possible to discriminate continuous structures that are three-dimensionally distributed from microstructures that are locally distributed, and generate and display a microstructure extracted image from which the microstructures are extracted in real time. The doctor views the microstructure extracted image to find a microstructure, which is hardly discriminated from a speckle pattern by eyes and appears in only a specific tomographic image, in a short time.

Further, the ultrasonic diagnostic apparatus according to this embodiment can arbitrarily set a frame of target image used for the microstructure extracting process and the size of the reference region. Therefore, it is possible to appropriately form the image of a microstructure according to the individual conditions by setting the size of the reference region and a frame of reference image in correspondence with the purpose of examination or an individual difference.

Furthermore, the ultrasonic diagnostic apparatus according to this embodiment can use various display modes, such as a display mode that displays the microstructure extracted image together with the body mark where the scanning range and the position of the ultrasonic probe when the target image is acquired are set, a display mode that displays the MIP image that is generated on the basis of the difference image obtained by the microstructure extracting process in a predetermined form, and a display mode that displays the images before and after the microstructure is extracted in a predetermined form. Therefore, the doctor observes the microstructure extracted image in a desired display form or compares the microstructure extracted images in various display forms to find a microstructure, which is hardly discriminated from a speckle pattern by eyes and appears in only a specific tomographic image, in a short time.

Furthermore, in this embodiment, a plurality of difference images are used to generate the MIP image. However, the invention is not limited thereto. For example, general images may be used to generate the MIP image.

(Fifth Embodiment)

In an ultrasonic diagnostic apparatus 1 according to a fifth embodiment, a predetermined speckle reduction process (a previous stage speckle reduction process) is performed on image group data, and then the microstructure extracting process according to the first embodiment is performed. Any process may be used as the previous stage speckle reduction process as long as it can remove at least one of a continuous structure and a speckle pattern (including a random speckle pattern). Specifically, the following methods may be used: three-dimensional CFAR (contrast false alarm rate) processing using image group data; two-dimensional CFAR processing corresponding to each two-dimensional image forming image group data; a spatial compounding method of overlapping signals that are transmitted or received in different directions to smooth a speckle pattern; and a similarity filtering method of using statistics to remove a speckle pattern.

Figure 19:
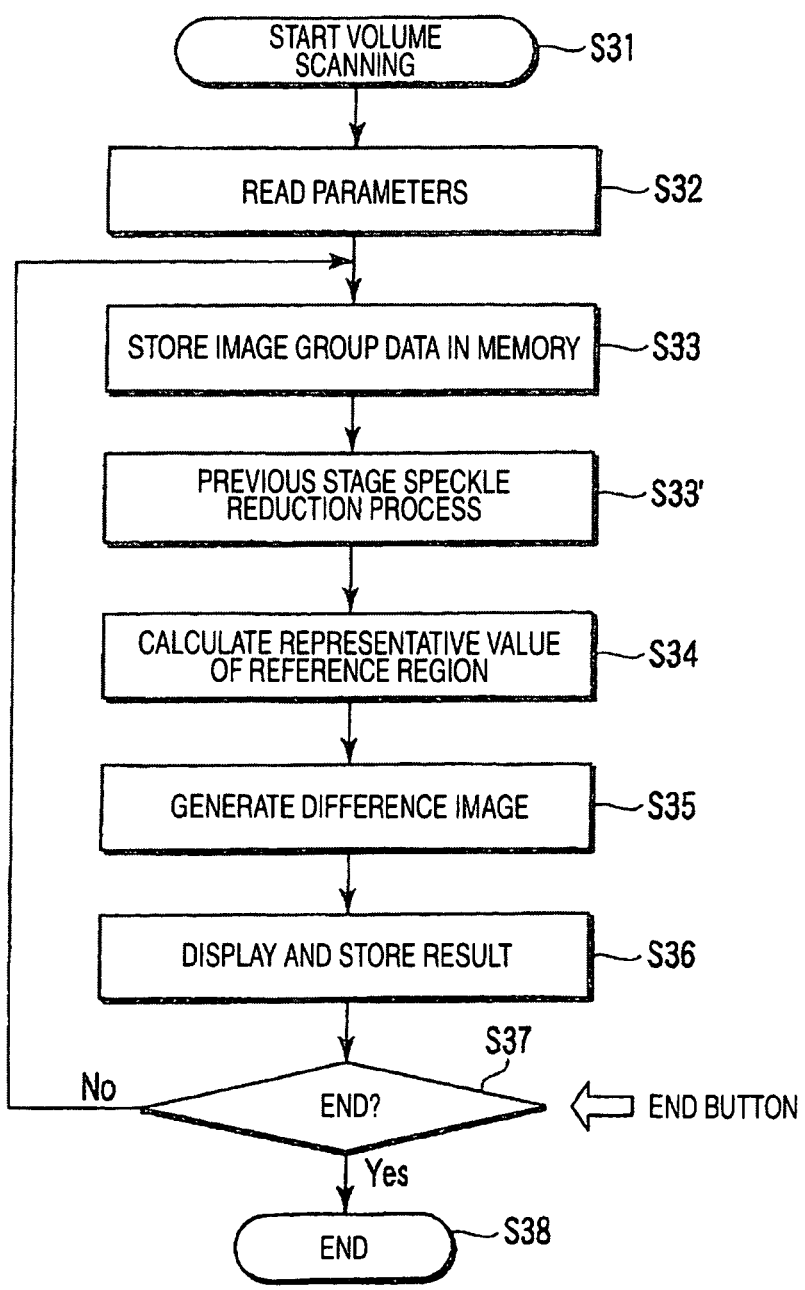
FIG. 19 is a flowchart illustrating the flow of a microstructure extracting process according to a fifth embodiment.

FIG. 19 is a flowchart illustrating the flow of the microstructure extracting process according to this embodiment. As shown in FIG. 19, first, when volume scanning starts, an instruction to change to the microstructure extracting process is issued, a necessary parameter group is read, and image group data related to the breast is acquired by volume scanning and is then stored in a memory (Steps S31, S32, and 33). Then, the image generating unit 25 performs the previous stage speckle reduction process on the image group data (Step S33') to calculates the representative value of the reference region of each reference image (Step S34), and performs the microstructure extracting process using the representative value to generate a plurality of difference images corresponding to the image group data (Step S35). The obtained difference images are displayed on the monitor 14 together with, for example, a body mark having the positional information of the ultrasonic probe, and are also automatically stored (Step S36).

According to the above-mentioned structure, it is possible to obtain the same effects as those in the first embodiment.

(Sixth Embodiment)

An ultrasonic diagnostic apparatus 1 according to a third embodiment performs the microstructure extracting process according to the first embodiment or the microstructure extracting process according to the second embodiment using a probe for a two-dimensional image having one-dimensional elements arranged therein, not a tilting probe for a three-dimensional image or a two-dimensional vibrator probe for a three-dimensional image. The structure of the ultrasonic diagnostic apparatus according to this embodiment is similar to that shown in FIG. 1 except that the ultrasonic probe 12 is a probe for a two-dimensional image. For clarity of description, in this embodiment, it is assumed that the ultrasonic diagnostic apparatus performs the microstructure extracting process according to the first embodiment.

Figure 20:
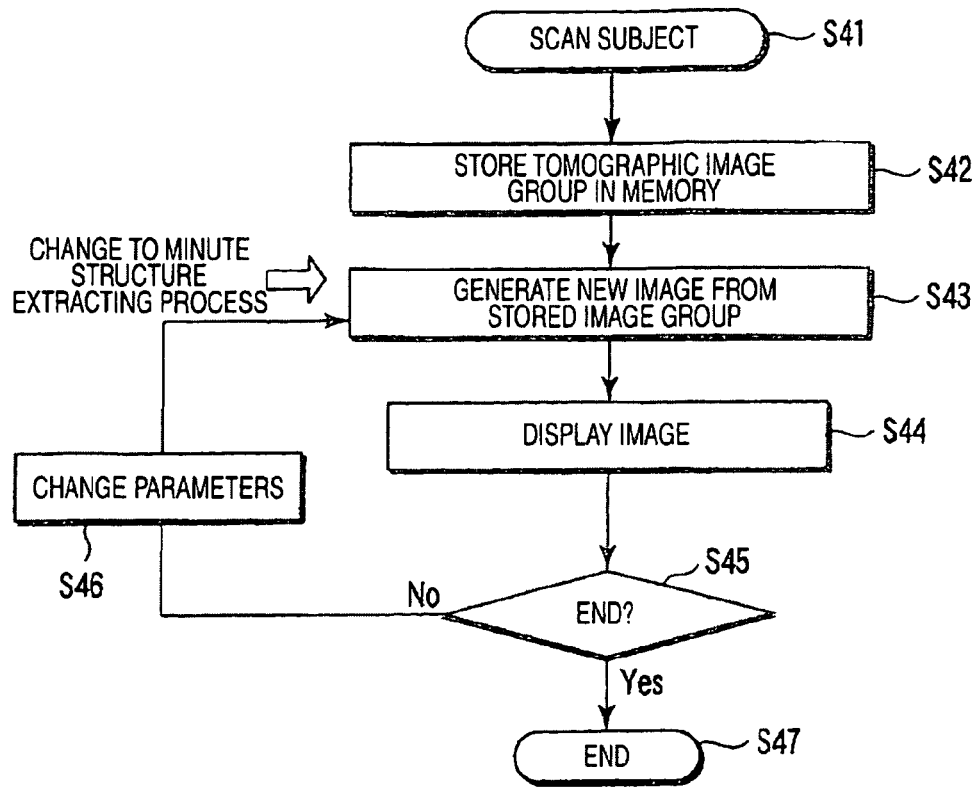
FIG. 20 is a flowchart illustrating the flow of a microstructure extracting process according to a sixth embodiment.

FIG. 20 is a flowchart illustrating the flow of the microstructure extracting process according to this embodiment. As shown in FIG. 20, first, scanning is performed on a subject (Step S41). In this case, it is premised that the operator acquires different tomographic images while slightly changing a scanning tomographic layer. These images are sequentially stored in a memory of the ultrasonic diagnostic apparatus (or a hard disk of the apparatus) (Step 42).

When the images are completely acquired, the microstructure extracting process is performed in response to instructions from the input device 13. At that time, a plurality of stored images are read, each of the above-mentioned processes (which are described in the first embodiment) is performed, and the processed result is displayed on the monitor 14 as a microstructure extracted image (Steps S43 and S44). The operator makes a proper diagnosis while viewing the new image, and then this flow ends (Step S45). Meanwhile, when appropriate diagnostic information is not obtained, parameters for microstructure extracting process are changed (Steps S45 and S46), and the processes of Steps S43 and S44 are repeated again on the basis of the changed parameters.

The ultrasonic diagnostic apparatus according to this embodiment acquires an ultrasonic image while slightly changing the scanning position of a probe for a two-dimensional image, and stores the image in its memory once. Then, the ultrasonic diagnostic apparatus reads the stored ultrasonic image and performs the microstructure extracting process using the read ultrasonic image. Therefore, it is possible to implement a microstructure extracting function even when the ultrasonic probe 12 cannot scan a three-dimensional region by electronic or mechanical control. In addition, since the microstructure extracted image is not obtained in real time, it is possible to use information of reference images arranged at both sides of a target image frame.

(Seventh Embodiment)

A seventh embodiment relates to an image processing apparatus that uses image group data obtained beforehand to perform the microstructure extracting process according to the fourth embodiment or the microstructure extracting process according to the fifth embodiment. The image processing apparatus may also be implemented by installing programs (microstructure extracting programs) for executing various processes related to the microstructure extracting function in a computer, such as a work station, and expanding these programs on a memory. In this case, these structure extracting programs may be stored on recording media, such as a magnetic disk, an optical disk, and a semiconductor memory, and then distributed.

Figure 21:
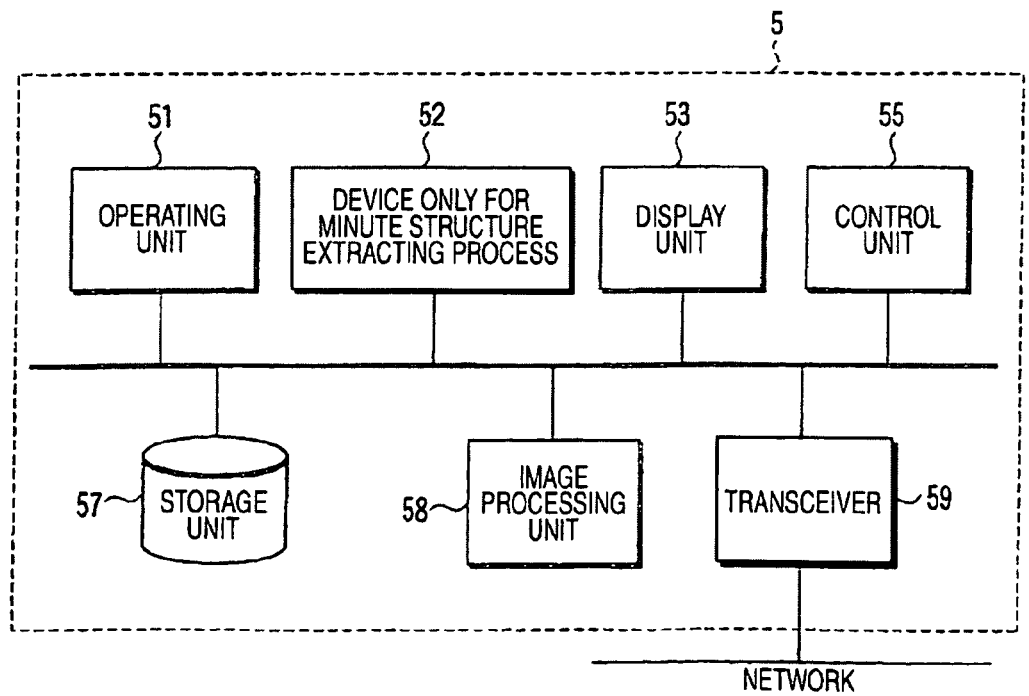
FIG. 21 is a block diagram illustrating the structure of an image processing apparatus 2 according to a seventh embodiment.

FIG. 21 is a block diagram illustrating the structure of an image processing apparatus 5 according to the seventh embodiment. As shown in FIG. 21, the image processing apparatus 5 includes an operating unit 51, a device 52 only for a microstructure extracting process, a display unit 53, a control unit 55, a storage unit 57, an image processing unit 58, and a transceiver 59.

The operating unit 51 includes a track ball, various types of switches, a mouse, and a keyboard that are used to input, for example, various instructions from the operator and conditions to the image processing apparatus 1.

The display unit 53 displays ultrasonic images (for example, a B-mode image and a microstructure extracted image) and an input screen for a predetermined operation in a predetermined form.

The control unit 5 dynamically or statically controls units of the image processing apparatus 5. In particular, the control unit 55 expands the microstructure extracting program stored in the storage unit 57 on its memory, and generally controls the display unit 53 and the image processing unit 58 according to the program.

The storage unit 57 stores the microstructure extracting program. In addition, the storage unit 57 stores, for example, image group data that is acquired by the transceiver 59 through a network or image data that is acquired from a detachable storage medium.

The image processing unit 58 performs the microstructure extracting process under the control of the control unit 55.

The transceiver 59 transmits or receives information including image data to or from an ultrasonic diagnostic apparatus or a picture achieving and communication system (PACS) server over a network.

Further, the image processing apparatus 5 includes the device 52 only for a microstructure extracting process. The device is not necessary to perform the microstructure extracting process in the image processing apparatus 5, but is used to improve operability in the subsequent microstructure extracting process. For example, the device may have the following structures.

Figure 22:
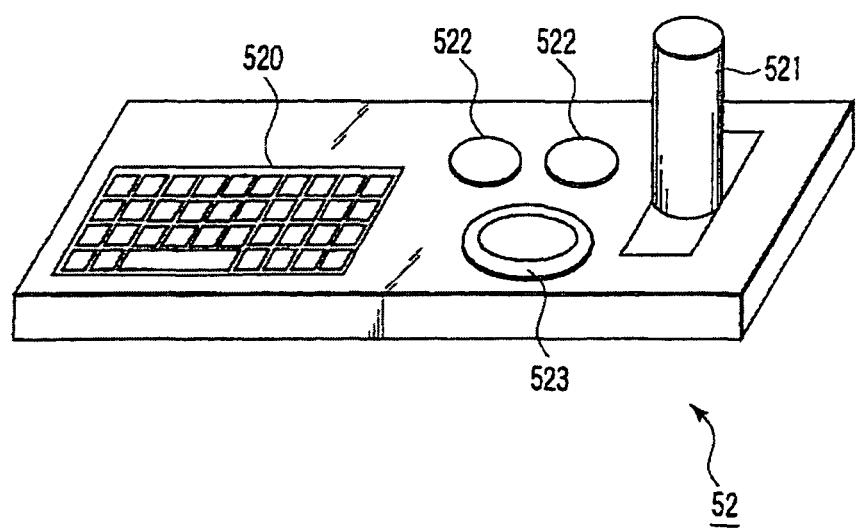
FIG. 22 is a diagram illustrating an example of a device 52 only for a microstructure extracting process.

FIG. 22 is a diagram illustrating an example of the device 52 only for a microstructure extracting process. As shown in FIG. 22, the device 52 only for a microstructure extracting process includes a keyboard 520 used for a general personal computer, an ultrasonic probe-shaped joy stick 521, buttons 522 only for the interpretation of tomographic images, and a track ball 523. The joy stick 521 is a lever type control tool that can be movable at least in the forward and backward directions, and can control the position of a frame displayed with respect to image data of a diagnostic image. Specifically, the reproduction, backward reproduction, frame advance reproduction, and fast-forward reproduction of a moving picture are operatively associated with the position of the joy stick 521 that is moved by the operator. The joy stick 521 preferably has the same shape as the ultrasonic probe. Therefore, the operator can play back a moving picture frame, return to several previous frames to check the frames again when finding a microstructure required for diagnosis (in general, since it takes some for the human to recognize an object, it is difficult for the operator to stop the moving picture at the same time when viewing it), stop the movement of the probe, and change the scanning direction with the same feeling as the user actually scans a subject, during the interpretation of tomographic images using a computer after scanning.

Further, the buttons 522 only for the interpretation of tomographic images have various functions for effectively interpreting the tomographic image subjected to the microstructure extracting process. For example, the buttons 522 include a button for switching the images displayed on the monitor, for example, the images before and after the microstructure extracting process. In addition, the buttons 522 include a button for separately storing a desired image frame as a still picture and a button for inputting explanatory nodes or arrows on the image. That is, the buttons are used to instruct the same operations as those in the diagnostic apparatus. Further, the track ball 523 is a pointer on the monitor, and it may be replaced with a mouse.

When the image processing apparatus 5 according to this embodiment is used to perform the microstructure extracting process according to the first embodiment, Steps S34 to S36 shown in FIG. 18 are performed on the image group data stored in the storage unit 57. When the image processing apparatus 5 according to this embodiment is used to perform the microstructure extracting process according to the second embodiment, Steps S33' to S36 shown in the figure are performed on the image group data stored in the storage unit 57.

According to the image processing apparatus of this embodiment, the microstructure extracting process according to the first or second embodiment can be performed in a terminal, such as a medical workstation, after scanning. In this case, the use of the device only for a microstructure extracting process makes it possible to display a microstructure extracted image with the same feeling as the operator stops the movement of the probe or changes the scanning direction during the actual scanning of a subject, during a post scanning process in which the operator interprets the captured image. As a result, the operator can effectively observe a proper microstructure extracted image with high operability. Therefore, it is possible to reduce the operating load of the operator, such as the doctor.

Next, an eighth embodiment of the invention will be described. In this embodiment, it is a necessary condition to acquire 'a thin slice sound field' and 'a plurality of tomographic images obtained by three-dimensional scanning'. First, the ultrasonic probe 12 will be described in detail below.

The ultrasonic probe 12 can be classified as follows by the type of array converters:

(1) a 1D array (a single row with only azimuth steering);

(2) a 1.25D array (multiple rows without electronic focusing in the elevation dimension);

(3) a 1.5D array (electronically focused but not steered in the elevation dimension);

(4) a 1.75D array (a large pitch array with limited three dimensional steering); and (5) a 2D array (a fine pitch array with a wide range of three dimensional steering).

Here, 'D' indicates a 'dimension', and since all of the arrays (2) to (5) are two-dimensionally arranged, they are referred to as 1.5D arrays. However, this expression is different from that defined by mathematics, but is commonly used in the ultrasonic diagnostic apparatus field. Among the arrays, the arrays (2) to (5) can form the thin slice sound field.

When the above-mentioned arrays are used to acquire a plurality of tomographic images, a method of slightly changing the position of a tomographic layer to acquire a plurality of tomographic images in a short time can be implemented by using the arrays (4) and (5) among the arrays. In addition, there is a method of using the arrays (1) to (5) to mechanically tilt vibrators, thereby acquiring three-dimensional information. This array is referred to as an array with a mechanical tiling mechanism. In this embodiment, it is preferable to use a '1.25D array with a mechanical tilting mechanism' or a '1.5D array with a mechanical tilting mechanism'. The 1.25D array will be described in detail below.

Figure 23:
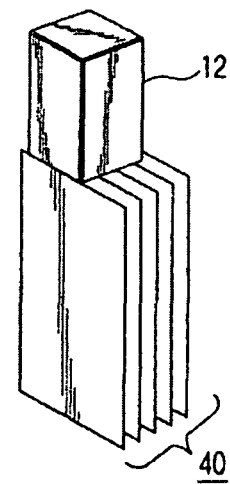
FIG. 23 is a diagram illustrating an example of acquiring a tomographic image group 40 including information of a three-dimensional region.

Next, the method of using the array to acquire an image will be described. First, one tomographic image is acquired by an ultrasonic wave radiated from the ultrasonic probe 12 by the same method as a general B-mode. A tomographic image different from the previous tomographic image is acquired by continuous electronic deflection or mechanical tilting. The same operation as described above is repeated to a tomographic image group 40 having information of a three-dimensional region, as shown in FIG. 23. FIG. 23 shows the tomographic images so as be recognizable, but actually, the distance between the tomographic images is very small. In addition, in the actual tiling operation, strictly, the tomographic layers of the tomographic images are not parallel to each other, but they may be considered to be parallel to each other when a fan angle is very small. In FIG. 23, five images are acquired, but it is preferable to acquire about three to 10 images.

In the diagram illustrating the structure of the ultrasonic diagnostic apparatus, the image synthesizing unit 27 superimposes the acquired tomographic image group on one image, and displays the result on the display unit as one tomographic image. For example, the following two methods can be used to synthesize the images.

(First Synthesizing Method: Maximum Brightness Projection Method)

In this method, the image synthesizing unit 27 assigns the maximum brightness of the pixels disposed at the same spatial position to the pixels at the corresponding positions in all the tomographic images of an image group, thereby obtaining one tomographic image.

According to the first synthesizing method, even when a microstructure is included in any of the tomographic images of the tomographic image group to be processed, the intensity of the detected echo signal of the microstructure becomes high by the effects of the thin slice sound field (that is, a small slice thickness) in addition to the effects of a reduction in speckle and the smoothing of a tissue structure by volume compounding. In addition, since there is a plurality of tomographic images having calcifications therein, it is possible to reduce the detection miss of microstructures even when the ultrasonic probe 12 or a subject is moved a little.

(Second Synthesizing Method: Representative Brightness Value Method)

Figure 24:
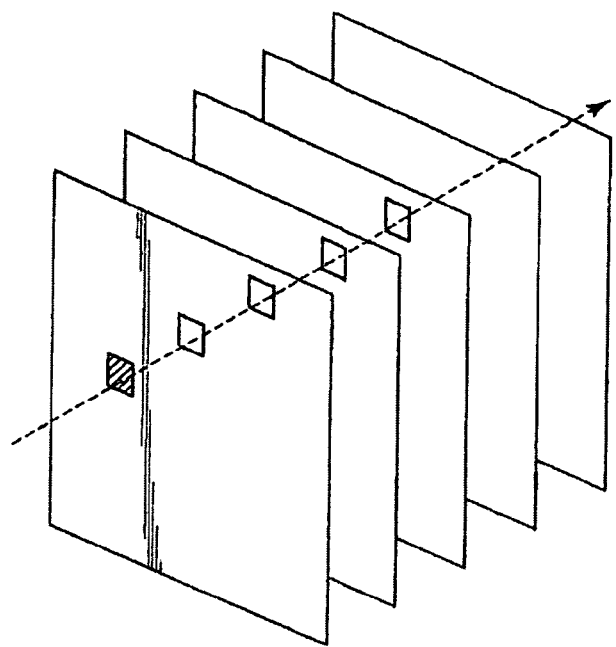
FIG. 24 is a diagram illustrating a second synthesizing method of detecting representative brightness from a plurality of acquired tomographic images.

In this method, first, as shown in FIG. 24, the image synthesizing unit 27 analyzes the brightness of pixels at coordinates corresponding to each tomographic layer. In this case, when a pixel with brightness that is considered unusual (hereinafter, referred to as 'unusual brightness', which will be described in detail below) is detected, the unusual brightness of the pixel is set to as a representative brightness value. When no unusual brightness is detected, the average brightness of all the pixels is set to as the representative brightness value, or the brightness of any of a plurality of tomographic images is set to the representative brightness value.

Figure 25A:
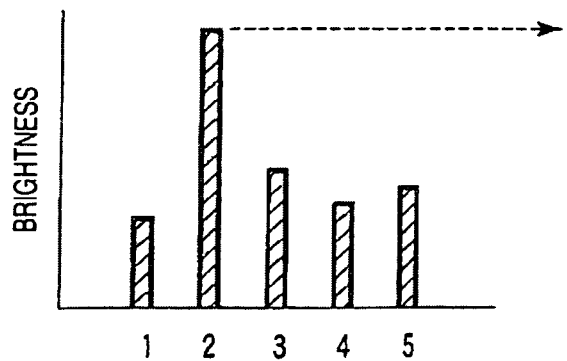
FIG. 25A is a conceptual diagram illustrating an algorithm for detecting the representative brightness.
Figure 25B:
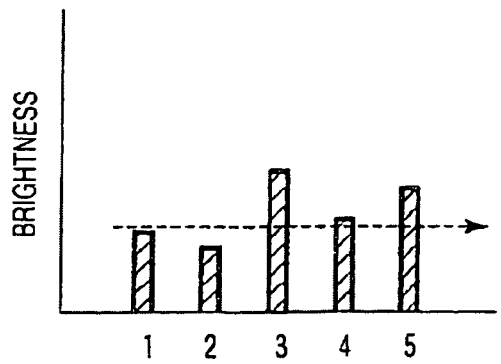
FIG. 25B is a conceptual diagram illustrating the algorithm for detecting the representative brightness.

FIG. 25A is a diagram illustrating an example of the method, and it is assumed that five target tomographic images are used. FIG. 25A shows the case when unusual brightness is detected, and FIG. 25B shows the case when no unusual brightness is detected. As shown in FIG. 25A, when unusual brightness is detected, the brightness level of the representative brightness value represented by a dotted arrow in FIG. 25A is coincide with the unusual brightness. As shown in FIG. 25B, when no unusual brightness is detected, the brightness level of the representative brightness value represented by a dotted arrow in FIG. 25B is coincide with the average brightness of all the pixels.

For example, the following method can be used to detect the unusual brightness.

(1) There is a method of detecting the unusual brightness using only a threshold value of brightness. An unusual brightness level is predetermined. In general, a gray-scale image has 256 gray-scale levels. When the maximum brightness level is set to 256, for example, the brightness of the pixel having a brightness level that is equal to or higher than 200 is set to the unusual brightness. When there is a plurality of unusual brightnesses, the highest brightness is used as the unusual brightness.

(2) First, the average value $\mu$ of the brightness values of target pixels and a standard deviation $\sigma$ thereof are calculated, and brightness statistically deviating from the standard deviation is used as the unusual brightness. For example, brightness that is equal to or higher than μ+3σ is used as the unusual brightness.

Here, image processing of regenerating new brightness using the unusual brightness or the average value is performed on all or some of the tomographic images. As a result, a new tomographic image is reconstructed and then displayed on the display unit.

Since a speckle pattern, which is an interference fringe, has a random amplitude, the maximum value corresponding to a mountain in the speckle pattern is detected at all time by the maximum brightness detecting method, which is the first synthesizing method. Therefore, a drawing performance deteriorates. This method solves this problem and improves a contrast ratio with a micro calcified portion.

Figure 26:
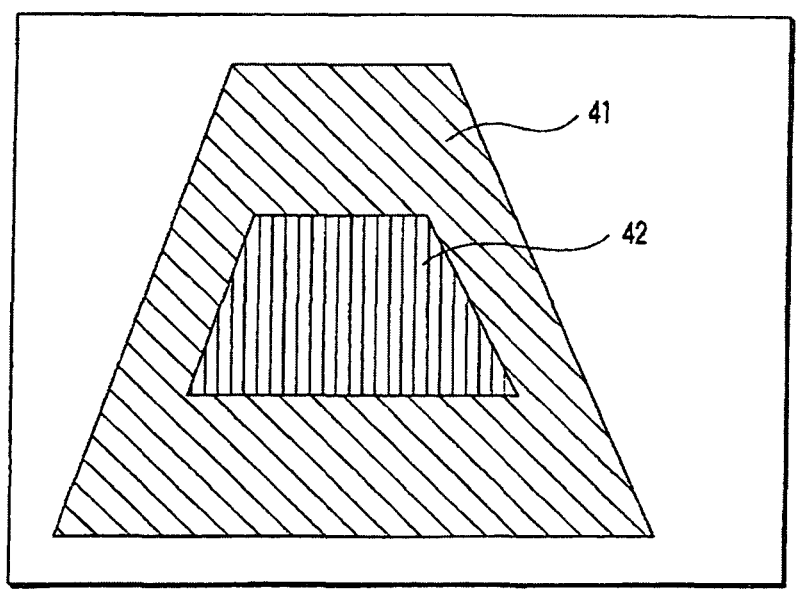
FIG. 26 is a diagram illustrating an ROI, which is a processing region to which an eighth embodiment is applied.

In the above-described embodiment, the above-mentioned process is performed on all the regions of a displayed image, but the invention is not limited thereto. For example, as shown in FIG. 26, when a region 41 of interest (ROI) is set on a diagnostic image, this embodiment can be applied to only the ROI. In this way, it is possible to reduce the processing time. In addition, the operator can use the input device to change the size and position of the ROI. Further, any one (for example, an image obtained in the first (or last) stage) of the plurality of obtained tomographic images may be display without any change as a region 42 other than the ROI.

As described above, according to this embodiment of the invention, it is possible to provide an ultrasonic diagnostic apparatus capable of allowing the operator to appropriately observe a microstructure, such as a micro calcified portion, which has been missed from the diagnosis of a breast cancer.

The invention is not limited to the above-described embodiments, but various modifications and changes of the invention can be made without departing from the scope and spirit of the invention. For example, the following modifications can be made.

The functions according to the above-described embodiments can be implemented by installing programs for executing the processes in a computer, such as a workstation, and expanding the programs on a memory. In this case, the programs for allowing the computer to execute the processes may be stored in a recording medium, such as a magnetic disk (for example, a floppy (registered trademark) disk or a hard disk), an optical disk (for example, CD-ROM or DVD), or a semiconductor memory, for distribution.

Further, various modifications can be made by appropriately combining a plurality of components according to the above-described embodiments. For example, some components may be removed from all the components according to the above-described embodiments. Furthermore, the components according to the above-described embodiments may be appropriately combined.

As described above, according to the invention, it is possible to provide an ultrasonic diagnostic apparatus and a method of controlling the ultrasonic diagnostic apparatus capable of exactly discriminating a continuous structure, such as the mammary gland, from a microstructure, such as a micro calcified portion, and extracting the microstructure.

What is claimed is:

1. An ultrasonic diagnostic apparatus comprising:
an ultrasonic wave transmitting/receiving unit that transmits an ultrasonic wave to a subject, receives a reflected wave of the ultrasonic wave, and generates echo signals of a plurality of frames on the basis of the received reflected wave;
an image data processor storing an algorithm that causes the image data processor to generate a data set composed of a plurality of two-dimensional images on the basis of the echo signals of the plurality of frames;
an image generating processor storing an algorithm that causes the image generating processor to generate a first image by performing a process of enhancing a microstructure included in the data set, the process of enhancing a microstructure including a microstructure extracting process setting a representative pixel value in a reference region using a first ultrasonic image included in the data set and a second ultrasonic image that is determined on the basis of a position of the first ultrasonic image, and setting a pixel value based on a comparison process in which a the representative pixel value in the reference region including pixels of the second ultrasonic image that spatially correspond to the pixels of the first ultrasonic image is compared with a target pixel value of the first ultrasonic image, thereby generating a microstructure extracted image; and
a display unit that displays the first image.

2. The ultrasonic diagnostic apparatus according to claim 1,
wherein the process of enhancing the microstructure included in the data set is signal processing of reducing a speckle pattern component included in the data set.

3. The ultrasonic diagnostic apparatus according to claim 2,
wherein the image generating processor performs the signal processing of reducing the speckle pattern component, using the relationship between pixels forming a predetermined two-dimensional image included in the data set and pixels forming another two-dimensional image included in the data set, to extract a microstructure included in the predetermined two-dimensional image, and
the image generating processor generates the first image including the microstructure.

4. The ultrasonic diagnostic apparatus according to claim 2,
wherein the signal processing of reducing the speckle pattern component is any one of CFAR (contrast false alarm rate) processing where a kernel pattern is three-dimensionally defined, a process using a statistical similarity filter, and a process using a spatial high-pass filter.

5. The ultrasonic diagnostic apparatus according to claim 2,
wherein the image generating processor performs the signal process of reducing the speckle pattern component on each of the plurality of two-dimensional images to extract pixels having values that are larger than a predetermined threshold value from each of the two-dimensional images,
the image generating processor performs a depth-direction arithmetic process for determining the relationship between the extracted pixels and the plurality of two-dimensional images to extract the microstructure included in the predetermined two-dimensional image included in the data set, and
the image generating processor generates the first image including the microstructure.

6. The ultrasonic diagnostic apparatus according to claim 5,
wherein the signal process of reducing the speckle pattern component is any one of CFAR (contrast false alarm rate) processing where a kernel pattern is two-dimensionally defined, a process using a statistical similarity filter, and a process using a spatial high-pass filter.

7. The ultrasonic diagnostic apparatus according to claim 5,
wherein the image generating processor performs the signal process of reducing the speckle pattern component on each of the plurality of two-dimensional images, and performs image processing in which a maximum value among the value of a pixel on each of the two-dimensional images and the values of adjacent pixels of the pixel is used as a new value of the pixel, and
after the image processing, the image generating processor performs the depth-direction arithmetic process.

8. The ultrasonic diagnostic apparatus according to claim 5,
wherein the image generating processor calculates a motion vector between the plurality of two-dimensional images, and performs a correcting process of correcting the positional deviation between the plurality of two-dimensional images on the basis of the calculated motion vector, and
after the correcting process, the image generating processor performs the depth-direction arithmetic process.

9. The ultrasonic diagnostic apparatus according to claim 2,
wherein the data set are acquired by an ultrasonic probe having a mechanism that tilts a plurality of ultrasonic vibrators for transmitting ultrasonic waves to the subject or an ultrasonic probe having the plurality of ultrasonic vibrators two-dimensionally arranged.

10. The ultrasonic diagnostic apparatus according to claim 1, further comprising:
a designating processor storing an algorithm that causes the designating processor to designate the second ultrasonic image among a plurality of ultrasonic images.

11. The ultrasonic diagnostic apparatus according to claim 1, wherein the image generating processor further comprises:
a designating processor storing an algorithm that causes the designating processor to perform the microstructure extracting process using each of a plurality of ultrasonic images and the first ultrasonic image to generate a plurality of the first images, and designates the second ultrasonic image on the basis of the total sum of the pixel values of the plurality of first images.

12. The ultrasonic diagnostic apparatus according to claim 1, further comprising:
a designating processor storing an algorithm that causes the designating processor to designate the size of the reference region.

13. The ultrasonic diagnostic apparatus according to claim 1,
wherein the number of second ultrasonic images is two that are symmetric with respect to the first ultrasonic image, and
the image generating processor performs the microstructure extracting process on each of the second ultrasonic images, and generates the microstructure extracted image on the basis of the processed result.

14. The ultrasonic diagnostic apparatus according to claim 1,
wherein the image generating processor performs the microstructure extracting process on the plurality of first ultrasonic images to generate a plurality of microstructure extracted images, and performs a maximum intensity projection process using the plurality of microstructure extracted images to generate a maximum intensity projection image, and
the display unit displays the maximum intensity projection image in a predetermined form.

15. The ultrasonic diagnostic apparatus according to claim 1,
wherein the image generating processor performs a predetermined process of removing the speckle pattern component on the first ultrasonic image, and performs the microstructure extracting process using the first ultrasonic image subjected to the predetermined process.

16. The ultrasonic diagnostic apparatus according to claim 1,
wherein the display unit displays a body mark including the position of the ultrasonic probe on the basis of information on the position of the ultrasonic probe attached to the first ultrasonic image.

17. The ultrasonic diagnostic apparatus according to claim 1, further comprising:
a designating processor storing an algorithm that causes the designating processor to designate the position of the first ultrasonic image in operative association with the spatial movement thereof, when the microstructure extracting process is performed.

18. The ultrasonic diagnostic apparatus according to claim 1,
wherein the image generating processor performs a microstructure extracting process of subtracting, from each of a plurality of pixels corresponding to a plurality of positions included in the three-dimensionally image data, the maximum pixel value in the reference region that is separated from each pixel by a predetermined distance, thereby generating the microstructure extracted image, and
the display unit displays the microstructure extracted image in a predetermined form.

19. The ultrasonic diagnostic apparatus according to claim 1,
wherein the ultrasonic wave transmitting/receiving unit three-dimensionally scans the subject while forming a thin sound field in a direction vertical to a tomographic image using vibrators that are two dimensionally arranged, thereby generating the echo signals of the plurality of frames in a direction that is parallel to the thin sound field, and
the image generating processor reconstructs a two-dimensional tomographic image using brightness information of the plurality of tomographic images, on the basis of the echo signals of the plurality of frames.

20. The ultrasonic diagnostic apparatus according to claim 19,
wherein the ultrasonic wave transmitting/receiving unit three-dimensionally scans the subject using an electronic delay circuit or a mechanical tilting mechanism, and the vibrators.

21. The ultrasonic diagnostic apparatus according to claim 19,
wherein the display unit displays the reconstructed two-dimensional tomographic image.

22. The ultrasonic diagnostic apparatus according to claim 19,
wherein the image generating processor performs a maximum intensity projection process on the plurality of tomographic images to generate the two-dimensional tomographic image.

23. The ultrasonic diagnostic apparatus according to claim 19,
wherein the image generating processor performs a statistical process on the brightnesses of corresponding pixels of the plurality of tomographic images, and uses a representative brightness value that is determined on the basis of the processed result as a pixel value to generate the two-dimensional tomographic image.

24. The ultrasonic diagnostic apparatus according to claim 1,
wherein the image generating processor performs the process of enhancing a microstructure including a subtraction process in which a maximum pixel value in a reference region including pixels of the second ultrasonic image that spatially correspond to the pixels of the first ultrasonic image is subtracted from the pixels of the first ultrasonic image, thereby generating a microstructure extracted image.

25. A method of controlling an ultrasonic diagnostic apparatus, the method comprising:
allowing the ultrasonic diagnostic apparatus to transmit an ultrasonic wave to a subject, receive a reflected wave of the ultrasonic wave, generate echo signals of a plurality of frames on the basis of the received reflected wave, generate a data set composed of a plurality of two-dimensional images on the basis of the echo signals of the plurality of frames;
allowing the ultrasonic diagnostic apparatus to generate a first image by performing a process of enhancing a microstructure included in the data set, the process of enhancing a microstructure including a microstructure extracting process setting a representative pixel in a reference region using a first ultrasonic image included in the data set and a second ultrasonic image that is determined on the basis of a position of the first ultrasonic image, and setting a pixel value based on a comparison process in which the representative pixel value in the reference region including pixels of the second ultrasonic image that spatially correspond to a target pixel value of the first ultrasonic image is compared with the pixels of the first ultrasonic image, thereby generating a microstructure extracted image; and
allowing the ultrasonic diagnostic apparatus to display the first image.

* * * * *